(12) United States Patent
Kirschenman et al.

(10) Patent No.: US 8,317,745 B2
(45) Date of Patent: Nov. 27, 2012

(54) ROBOTIC CATHETER ROTATABLE DEVICE CARTRIDGE

(75) Inventors: Mark B. Kirschenman, Waverly, MN (US); Troy T. Tegg, Elk River, MN (US); John A. Hauck, Shoreview, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 908 days.

(21) Appl. No.: 12/347,842

(22) Filed: Dec. 31, 2008

(65) Prior Publication Data

US 2009/0247944 A1   Oct. 1, 2009

Related U.S. Application Data

(60) Provisional application No. 61/040,143, filed on Mar. 27, 2008, provisional application No. 61/099,904, filed on Sep. 24, 2008.

(51) Int. Cl.
*A61M 31/00* (2006.01)
(52) U.S. Cl. ..................................... 604/95.04
(58) Field of Classification Search ............... 604/95.04, 604/95.05, 264, 22; 606/41, 130; 424/422; 318/568.11; 600/145; 607/122
See application file for complete search history.

(56) References Cited

U.S. PATENT DOCUMENTS

| | | | |
|---|---|---|---|
| 4,802,487 A | 2/1989 | Martin et al. | |
| 4,884,557 A | 12/1989 | Takehana et al. | |
| 5,170,817 A | 12/1992 | Sunderland | |
| 5,318,525 A | 6/1994 | West et al. | |
| 5,441,483 A | 8/1995 | Avitall | |
| 5,545,200 A | 8/1996 | West et al. | |
| 5,579,442 A | 11/1996 | Kimoto et al. | |
| 5,630,783 A | 5/1997 | Steinberg | |
| 5,706,827 A | 1/1998 | Ehr et al. | |
| 5,791,908 A | 8/1998 | Gillio | |
| 5,807,377 A | 9/1998 | Madhani et al. | |
| 5,808,665 A | 9/1998 | Green | |
| 6,040,758 A | 3/2000 | Sedor et al. | |
| 6,063,095 A | 5/2000 | Wang et al. | |
| 6,348,911 B1 | 2/2002 | Rosenberg et al. | |
| 6,396,232 B2 | 5/2002 | Haanpaa et al. | |
| 6,500,167 B1 | 12/2002 | Webster | |
| 6,709,667 B1 | 3/2004 | Lowe et al. | |

(Continued)

FOREIGN PATENT DOCUMENTS

WO   WO-2008/101228   8/2008

(Continued)

OTHER PUBLICATIONS

"International Search Report & Written Opinion", PCT/US2009/069712 Feb. 25, 2010.

(Continued)

*Primary Examiner* — Nicholas Lucchesi
*Assistant Examiner* — Brooke Matney
(74) *Attorney, Agent, or Firm* — Dykema Gossett PLLC

(57) ABSTRACT

A robotic catheter rotatable device cartridge may include a housing member attachable to a drive mechanism for rotating the cartridge and a catheter attached to the cartridge along an axial direction of the catheter. A slider block may be generally slidable relative to the housing and engaged with one or more steering wires for controlling movement of the catheter in a transverse direction relative to the axial direction. The catheter may include the steering wire(s) engaged therewith and movable in the transverse direction when the slider block is linearly driven in a predetermined direction.

16 Claims, 28 Drawing Sheets

U.S. PATENT DOCUMENTS

| | | |
|---|---|---|
| 6,850,252 B1 | 2/2005 | Hoffberg |
| 6,869,390 B2 | 3/2005 | Elliott et al. |
| 6,869,396 B2 | 3/2005 | Belson |
| 7,199,790 B2 | 4/2007 | Rosenberg et al. |
| 7,276,044 B2 | 10/2007 | Ferry et al. |
| 2002/0068868 A1 | 6/2002 | Thompson et al. |
| 2002/0072704 A1 | 6/2002 | Mansouri-Ruiz |
| 2002/0087048 A1 | 7/2002 | Brock et al. |
| 2004/0193239 A1 | 9/2004 | Falwell et al. |
| 2005/0075538 A1 | 4/2005 | Banik et al. |
| 2005/0203382 A1 | 9/2005 | Govari et al. |
| 2006/0089637 A1 | 4/2006 | Werneth et al. |
| 2006/0155321 A1 | 7/2006 | Bressler et al. |
| 2006/0276775 A1 | 12/2006 | Rosenberg et al. |
| 2006/0293643 A1 | 12/2006 | Wallace et al. |
| 2007/0043338 A1 | 2/2007 | Moll et al. |
| 2007/0142726 A1 | 6/2007 | Carney et al. |
| 2007/0185486 A1 | 8/2007 | Hauck et al. |
| 2007/0197896 A1 | 8/2007 | Moll et al. |
| 2007/0197939 A1 | 8/2007 | Wallace et al. |
| 2007/0198008 A1 | 8/2007 | Hauck et al. |
| 2007/0233044 A1 | 10/2007 | Wallace et al. |
| 2007/0270685 A1 | 11/2007 | Kang et al. |
| 2007/0298877 A1 | 12/2007 | Rosenberg et al. |
| 2008/0009791 A1 | 1/2008 | Cohen et al. |
| 2008/0013809 A1 | 1/2008 | Zhu et al. |
| 2008/0312536 A1 | 12/2008 | Dala-Krishna |
| 2009/0033623 A1 | 2/2009 | Lin |
| 2009/0247993 A1 | 10/2009 | Kirschenman et al. |
| 2009/0322697 A1 | 12/2009 | Cao |

FOREIGN PATENT DOCUMENTS

| | | |
|---|---|---|
| WO | WO-2009/120992 | 10/2009 |

OTHER PUBLICATIONS

Massey, Joe B. et al., "Medical device introduction systems and methods", WO 2007-146325 A2 Dec. 21, 2007.

Morales, Ruiz, "Robotic surgical system for performing minimally invasive medical procedures", WO 2007-088208 Aug. 9, 2007.

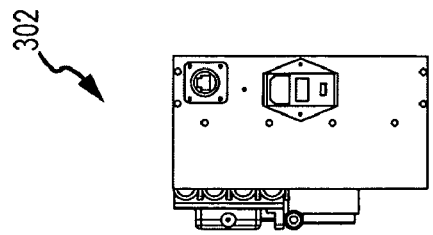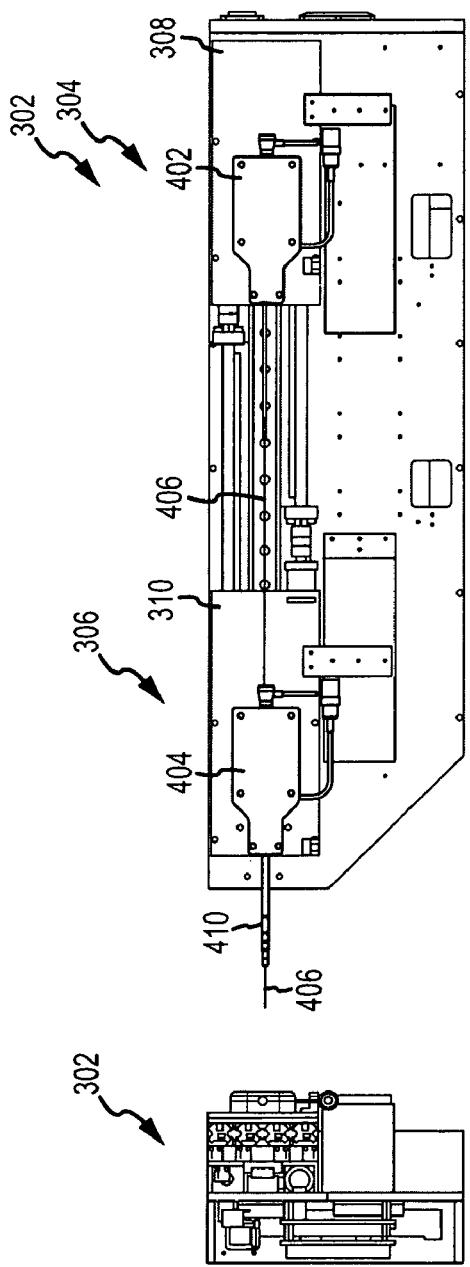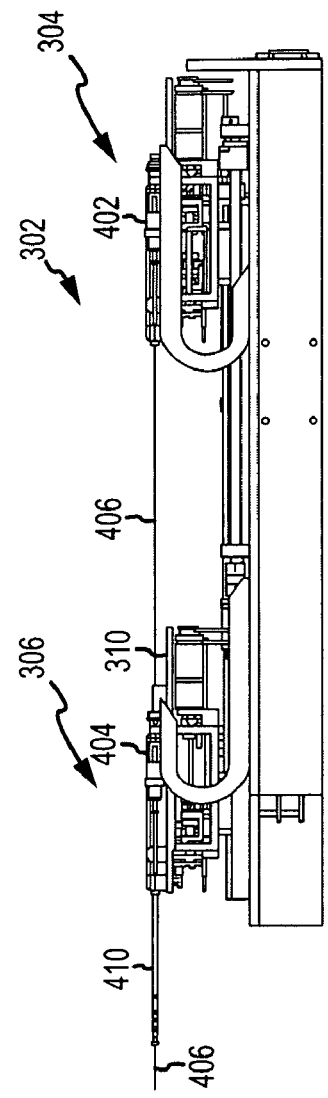
FIG.3e
FIG.3f
FIG.3g
FIG.3d

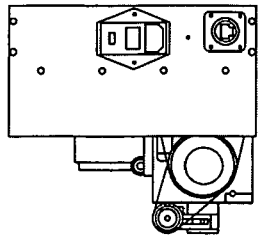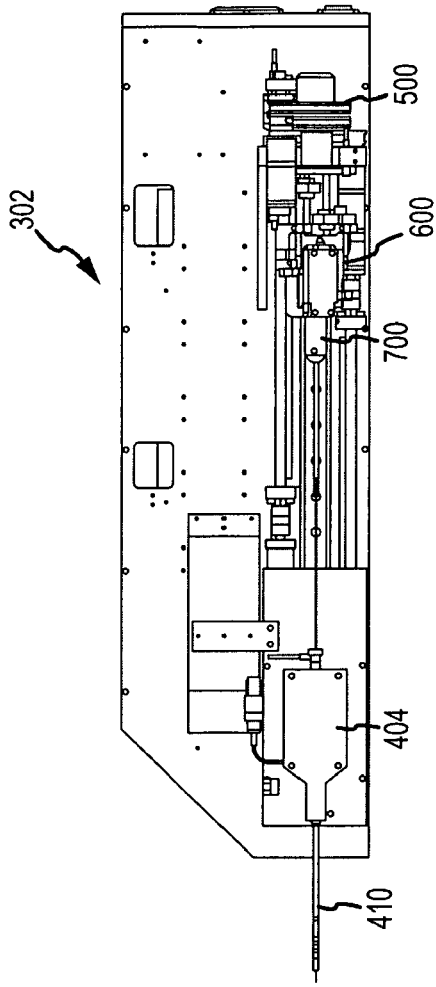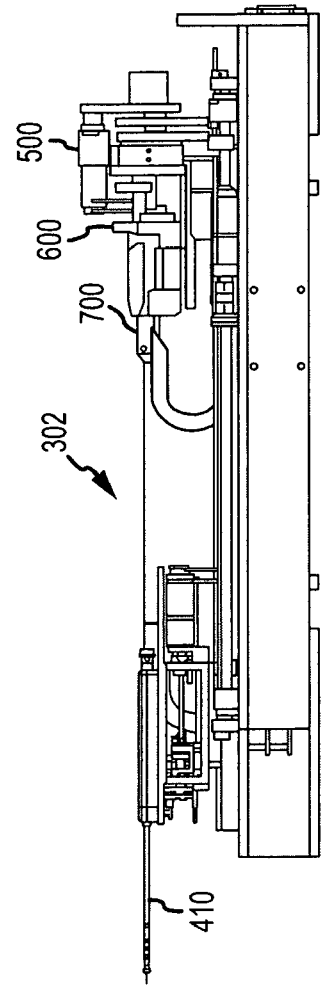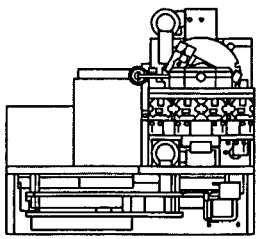

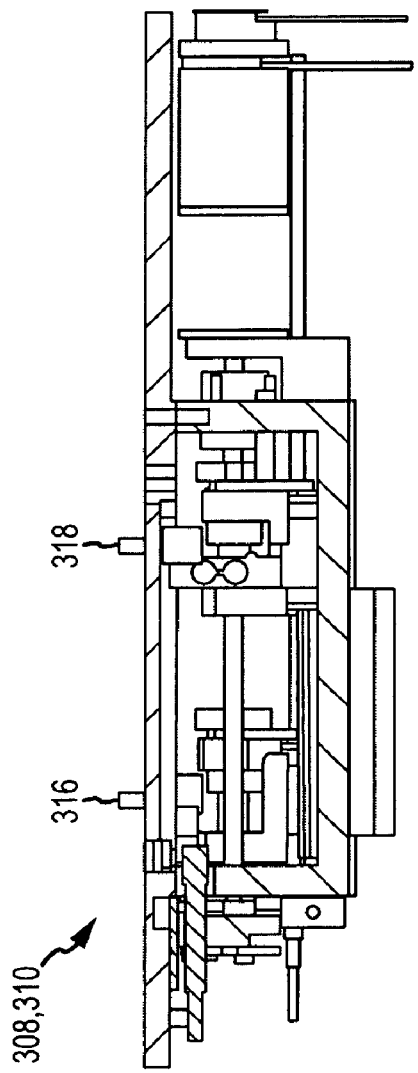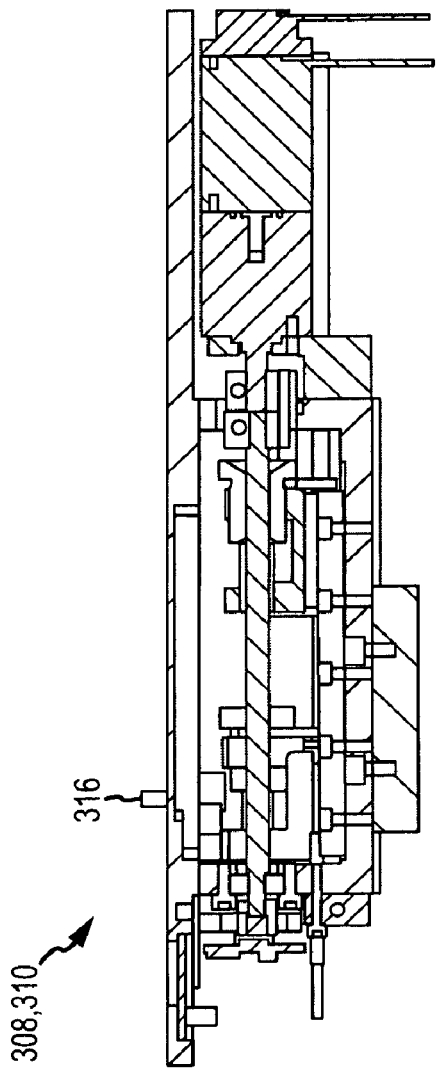

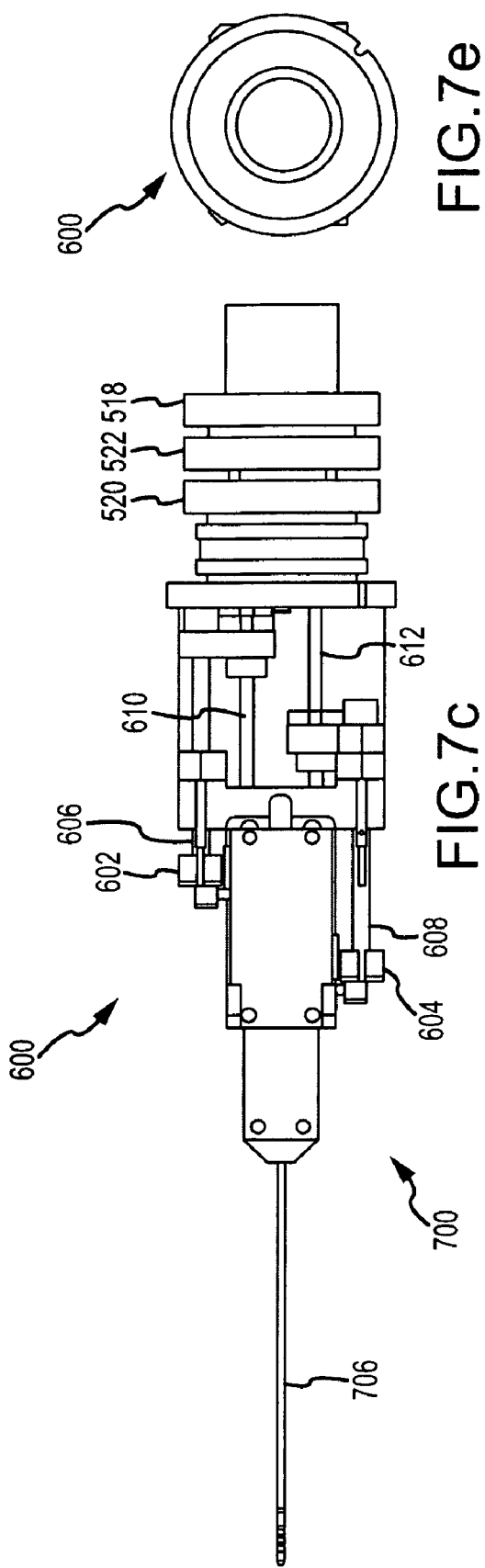
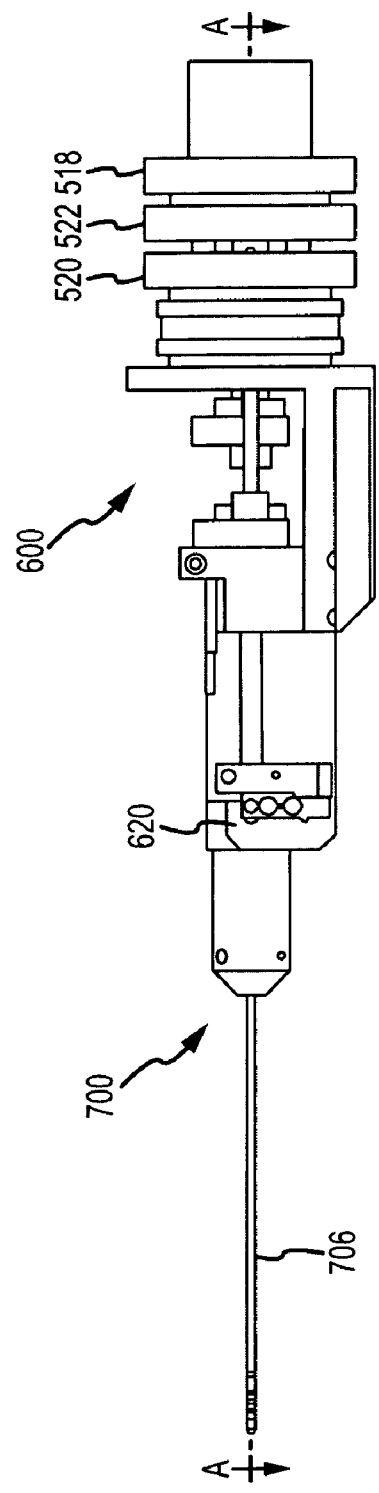

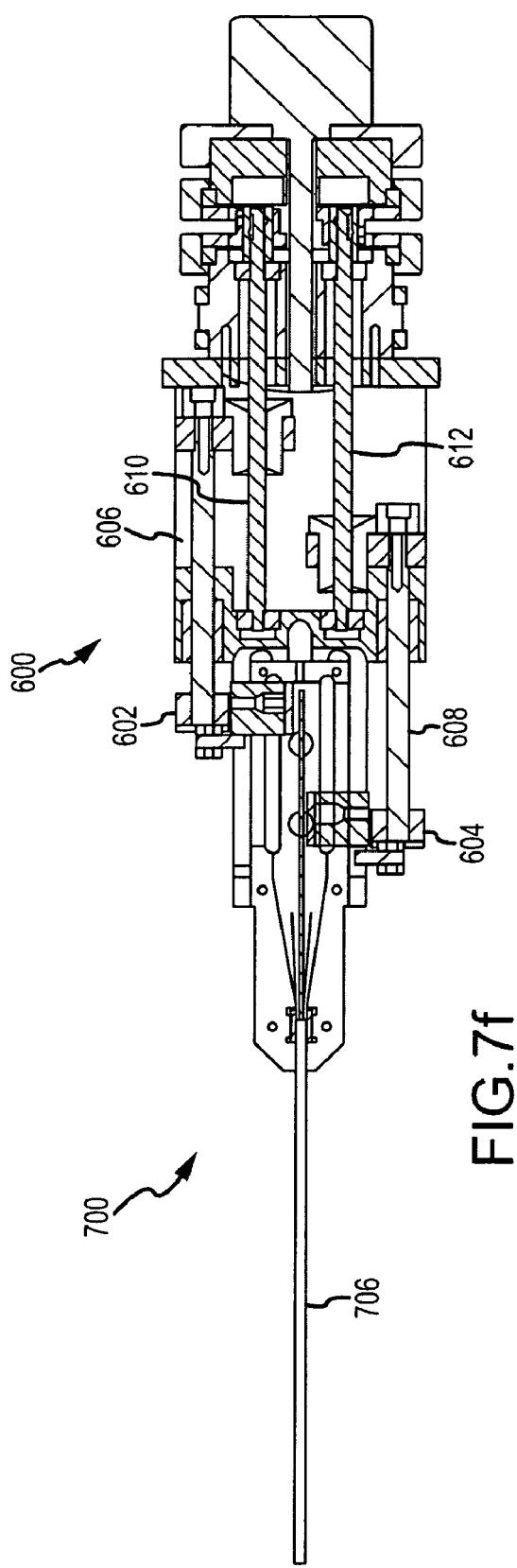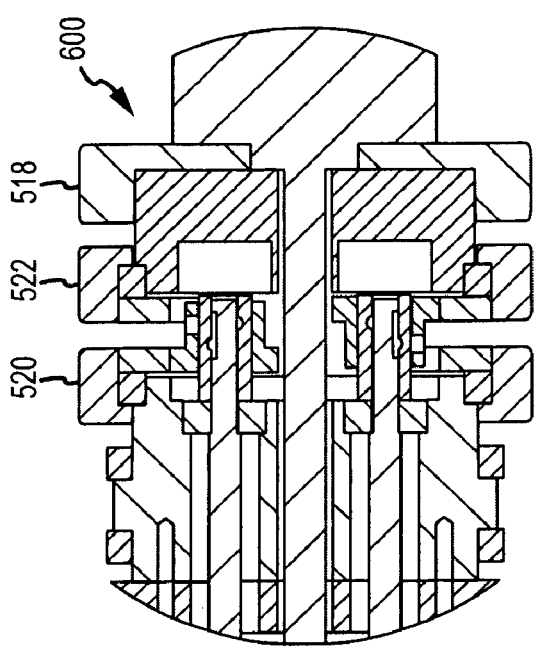

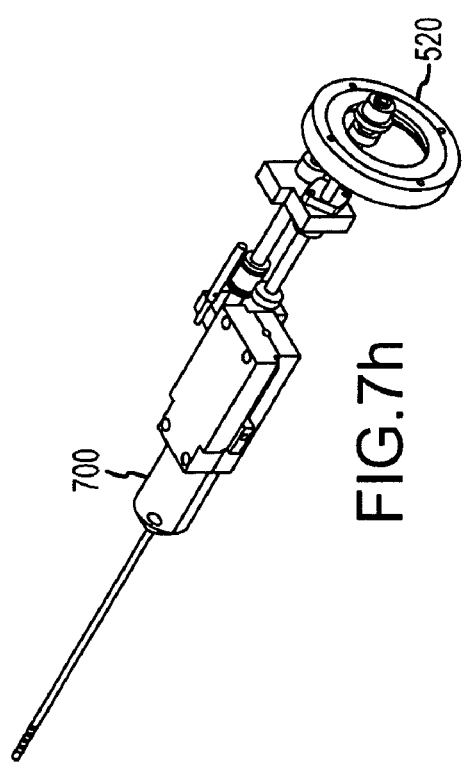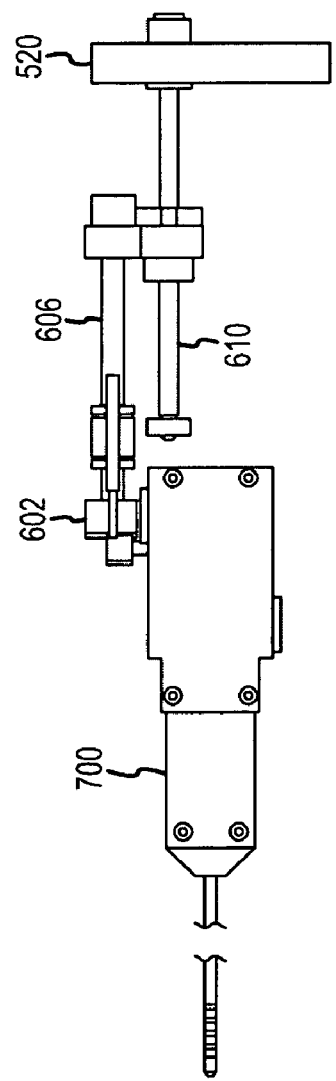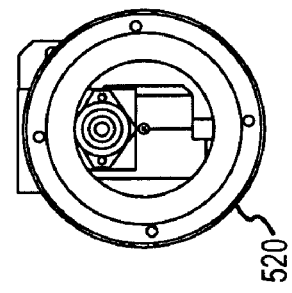

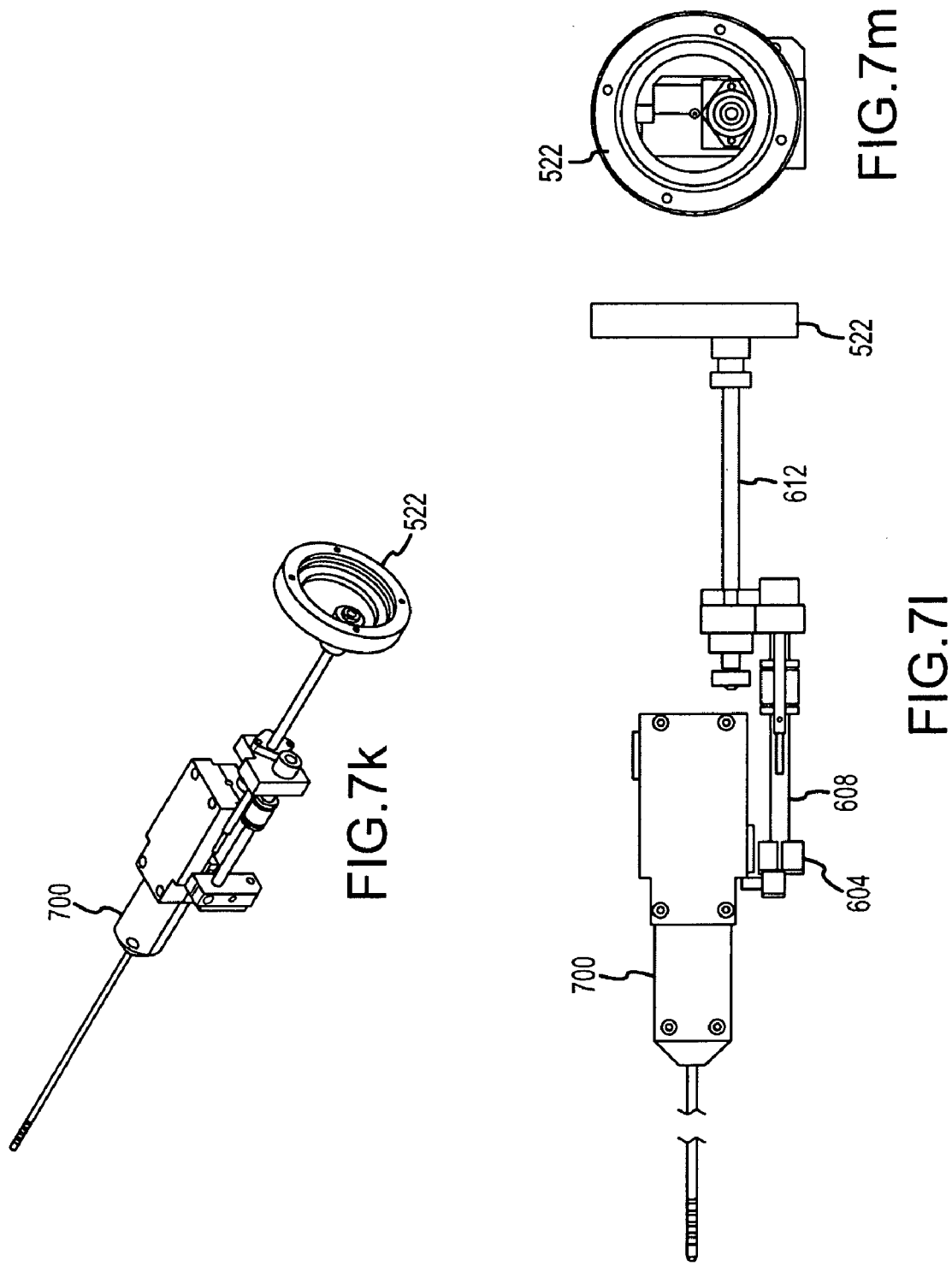

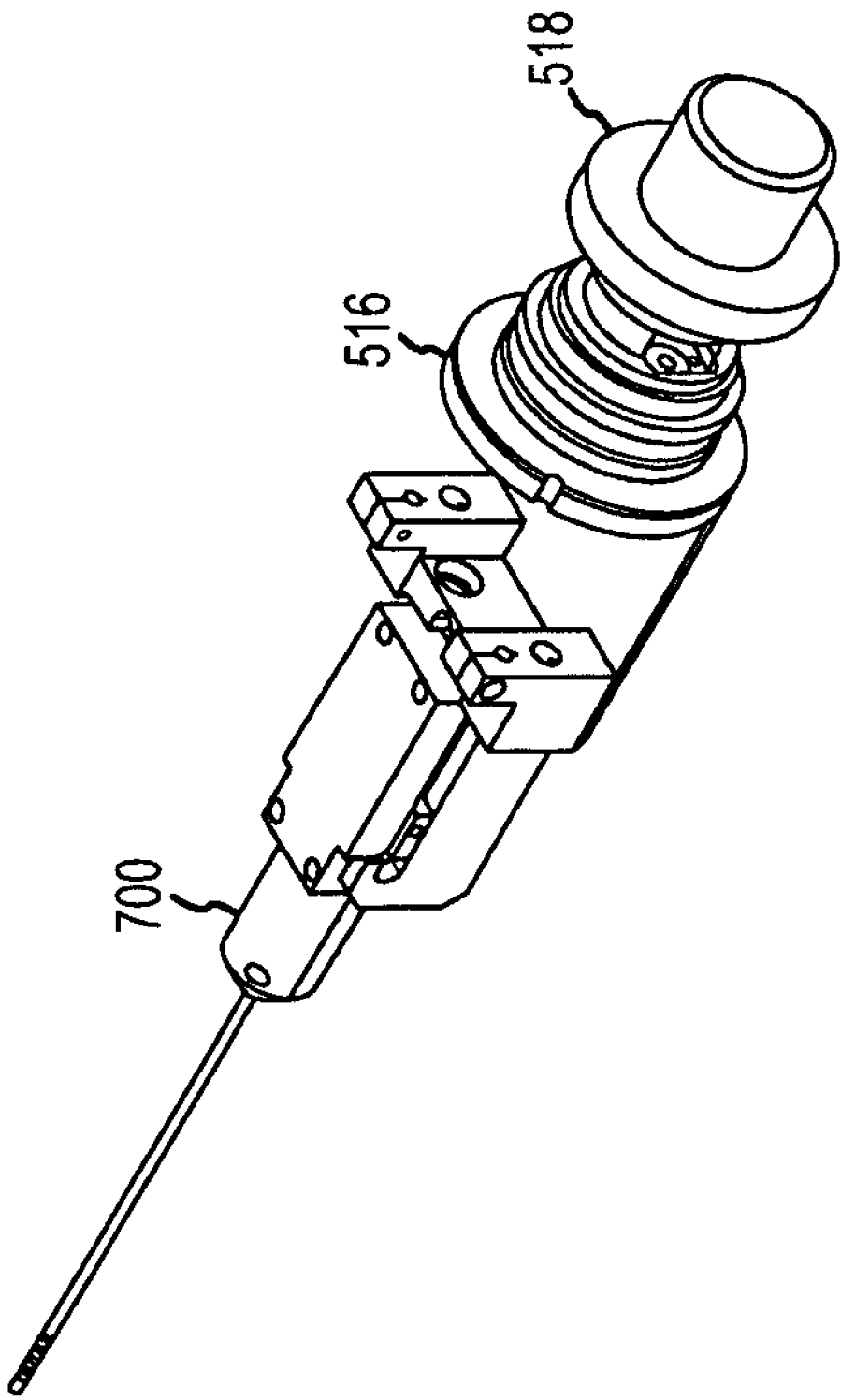

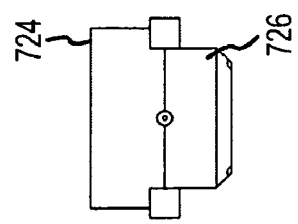
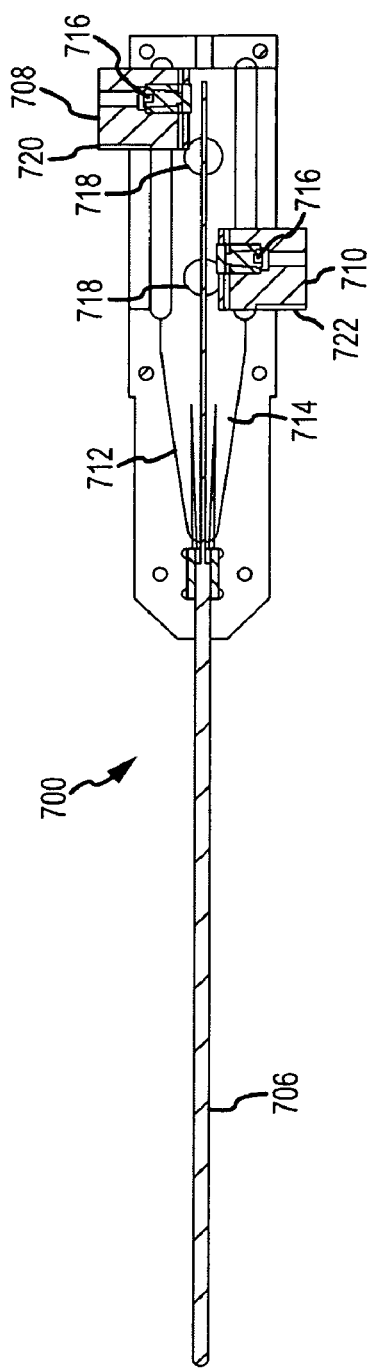
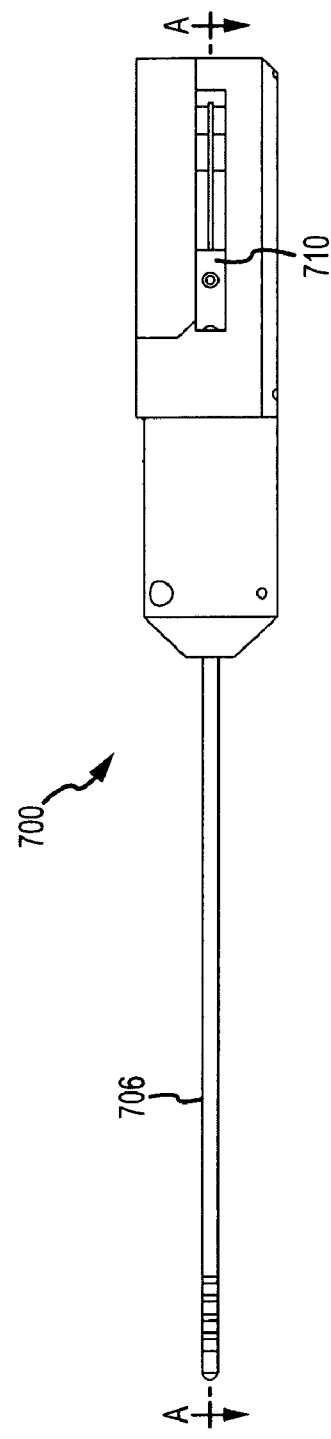

ROBOTIC CATHETER ROTATABLE DEVICE CARTRIDGE

CROSS REFERENCE TO RELATED APPLICATIONS

This application claims the benefit of priority to U.S. Provisional Application Nos. 61/040,143, filed Mar. 27, 2008 and 61/099,904, filed Sep. 24, 2008, the entire disclosures of which are incorporated herein by reference.

BACKGROUND OF THE INVENTION a. Field of the Invention

This invention relates to a robotic catheter system and method for automated control of a catheter and related components. In particular, the instant invention relates to a removable robotic rotatable device cartridge usable with a robotic catheter system for manipulating a catheter and related components, for example, for diagnostic, therapeutic, mapping and ablative procedures.

b. Background Art

Electrophysiology catheters are used in a variety of diagnostic and/or therapeutic medical procedures to correct conditions such as atrial arrhythmia, including for example, ectopic atrial tachycardia, atrial fibrillation, and atrial flutter. Arrhythmia can create a variety of dangerous conditions including irregular heart rates, loss of synchronous atrioventricular contractions and stasis of blood flow which can lead to a variety of ailments and even death.

Typically in a procedure, a catheter is manipulated through a patient's vasculature to, for example, a patient's heart, and carries one or more electrodes which may be used for mapping, ablation, diagnosis, or other treatments. Once at the intended site, treatment may include radio frequency (RF) ablation, cryoablation, lasers, chemicals, high-intensity focused ultrasound, etc. An ablation catheter imparts such ablative energy to cardiac tissue to create a lesion in the cardiac tissue. This lesion disrupts undesirable electrical pathways and thereby limits or prevents stray electrical signals that lead to arrhythmias. As readily apparent, such treatment requires precise control of the catheter during manipulation to and at the treatment site, which can invariably be a function of a user's skill level.

The inventors herein have thus recognized a need for a system and method for precise and dynamic automated control of a catheter and its related components, for example, for diagnostic, therapeutic, mapping and ablative procedures, that will minimize and/or eliminate procedural variability due to a user's skill level. The inventors herein have also recognized a need for a system and method for performing user-specified procedures at the patient site or from a remote location.

BRIEF SUMMARY OF THE INVENTION

It is desirable to provide a system and method for precise and dynamic automated control of a catheter and its related components. In particular, it is desirable to provide a system and method for precise and dynamic automated control, for example, for diagnostic, therapeutic, mapping and ablative procedures, that will minimize and/or eliminate procedural variability due to a user's skill level, with the procedures being optionally performed at the patient site or from a remote location.

A system and method for precise and dynamic automated control of a catheter and its related components may include a robotic catheter rotatable device cartridge that eliminates backlash, "slop" and other discontinuities in catheter and sheath control that can make computer control thereof difficult. The system and method, as discussed herein, may generally include a linear mechanism between the drive means and catheter tip, as opposed to a rotary system which operates on the radius change of a wire for controlling a catheter tip, thus significantly enhancing the overall control function.

A system and method for precise and dynamic automated control of a catheter and its related components may include a robotic catheter rotatable device cartridge including a housing member attachable to a drive mechanism for rotating the cartridge and a catheter attached to the cartridge along an axial direction of the catheter. One or more slider blocks may be generally slidable relative to the housing and engaged with one or more steering wires for controlling movement of the catheter in a transverse direction relative to the axial direction. The catheter may include the steering wire engaged therewith and movable in the transverse direction when the slider block is linearly driven in a predetermined direction.

For the robotic catheter rotatable device cartridge described above, in one embodiment, the housing may be removably attachable to a drive head for rotatable attachment to the drive mechanism, and the slider block may be engageable with a drive head mount for linear driving of the slider block. In one embodiment, a magnetic mount may be provided in the housing or the drive head for engagement with a complementary surface on the other one of the housing or the drive head for releasable locking of the cartridge with the drive head. In one embodiment, one or more recesses may be provided in the housing or the drive head for engagement with one or more complementary locking detents on the other one of the housing or the drive head for releasable locking of the cartridge with the drive head.

For the robotic catheter rotatable device cartridge described above, in one embodiment, two steering wires may be provided for controlling movement of the catheter in generally opposing transverse directions. In one embodiment, the slider block may be linearly driveable to pull the steering wire generally linearly along a length of the steering wire.

A system and method for precise and dynamic automated control of a catheter and its related components may include a robotic catheter rotatable device cartridge including a housing member attachable to a drive mechanism for rotating the cartridge and a surgically insertable device attached to the cartridge generally along an axial direction of the surgically insertable device. One or more first elements may be generally linearly movable along the housing and engaged with one or more steering wires for controlling movement of the surgically insertable device in a transverse direction relative to the axial direction. The surgically insertable device may include the steering wire engaged therewith and be movable in the transverse direction when the first element is linearly driven in a predetermined direction.

For the robotic catheter rotatable device cartridge described above, in one embodiment, the housing may be removably attachable to a drive head for rotatable attachment to the drive mechanism, and the first element may be engageable with a second element on the drive head for linear driving of the first element. In one embodiment, the robotic catheter rotatable device cartridge may include one or more first engageable members on the housing or the drive head for engagement with one or more complementary engageable member on the other one of the housing or the drive head for releasable locking of the cartridge with the drive head. In one embodiment, one or more magnetic mounts may be provided in the housing or the drive head for engagement with a complementary surface on the other one of the housing or the drive head for releasable locking of the cartridge with the drive head.

For the robotic catheter rotatable device cartridge described above, in one embodiment, two steering wires may be provided for controlling movement of the surgically insertable device in generally opposing transverse directions. In one embodiment, the first element may be linearly driveable to pull the steering wire generally linearly along a length of the steering wire. In one embodiment, the first element may be a slider block linearly slidable along a channel on or in the housing. In one embodiment, the surgically insertable device may be a catheter, a sheath or a transseptal needle. The linear moveability of the first element, in one embodiment, may generally eliminate any backlash or discontinuities during driving of the surgically insertable device. In one embodiment, the cartridge may be infinitely rotatable. In one embodiment, the robotic catheter rotatable device cartridge may include integrated force sensors operatively connected to the cartridge for permitting active tensioning of the steering wire for controlling movement of the surgically insertable device. The robotic catheter rotatable device cartridge, in one embodiment, may include integrated force sensors operatively connected to the cartridge for limiting stress on the surgically insertable device by limiting movement of the cartridge.

The foregoing and other aspects, features, details, utilities and advantages of the present invention will be apparent from reading the following description and claims, and from reviewing the accompanying drawings.

BRIEF DESCRIPTION OF THE DRAWINGS

FIGS. 3d-3i are respectively enlarged left side, right side, top, front, back and a corresponding left side view of a first embodiment of a robotic catheter manipulator assembly, and FIGS. 3j-3m are respectively enlarged left side, right side, top and front views of the robotic catheter manipulator assembly of FIG. 3a, illustrating use of the manipulator assembly with a robotic catheter rotatable device cartridge;

FIGS. 4d-4g are respectively enlarged top and right side, and respectively sections A-A and B-B taken generally along lines A-A and B-B in FIG. 4d, of a first embodiment of a manipulation base;

FIGS. 7c-7e are top, front and side, FIG. 7f is section A-A taken generally along line A-A in FIG. 7d, FIG. 7g is an enlarged area of FIG. 7f, and FIGS. 7h-7n are drive layout views of a robotic catheter rotatable drive head, with FIGS. 3j-3m illustrating an exemplary usage of the robotic catheter rotatable drive head;

FIGS. 8a-8c are enlarged isometric, front and side, and FIG. 8d is section A-A taken generally along line A-A in FIG. 8b, views of a robotic catheter rotatable device cartridge, with FIGS. 3j-3m illustrating an exemplary usage of the robotic catheter rotatable device cartridge;

DETAILED DESCRIPTION OF EMBODIMENTS OF THE INVENTION

Figure 1:
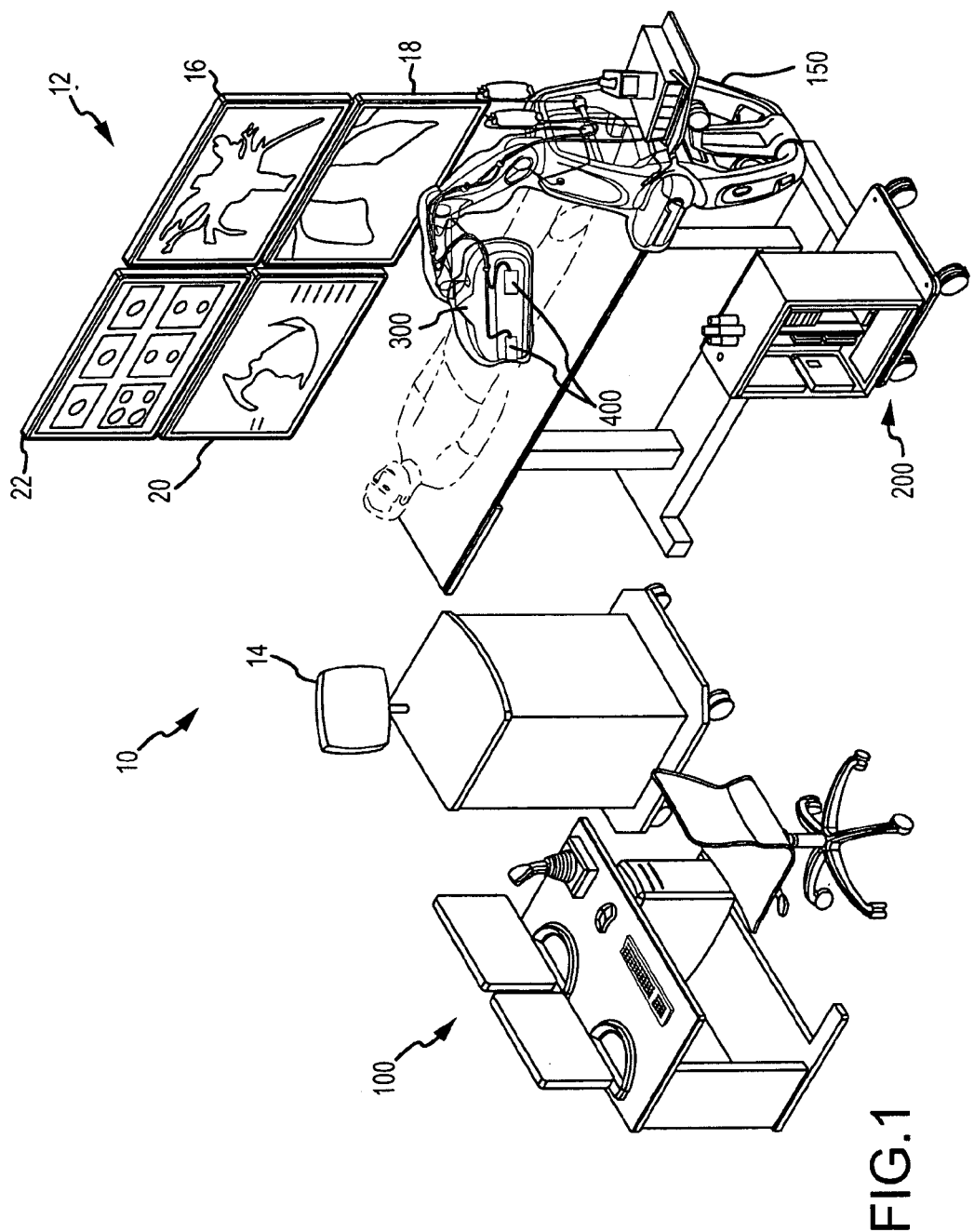
FIG. 1 is an isometric diagrammatic view of a robotic catheter system, illustrating an exemplary layout of various system components.

Referring now to the drawings wherein like reference numerals are used to identify identical components in the various views, an embodiment of robotic catheter system 10 (described in detail in commonly owned and copending application titled "Robotic Catheter System"), also referred to as "the system," may be likened to power steering for a catheter system. The system may be used, for example, to manipulate the location and orientation of catheters and sheaths in a heart chamber or in another body cavity. As shown in FIG. 1 and described in detail below, robotic catheter system 10 may generally incorporate a human input device and control system (referred to as "input control system") 100, e.g., a joystick and related controls (described in detail in commonly owned and copending applications titled "Robotic Catheter System Input Device" and "Robotic Catheter System Including Haptic Feedback"), that a user such as an electrophysiologist (EP) may interact with, an electronic control system 200 (described in detail in commonly owned and copending application titled "Robotic Catheter System with Dynamic Response") that translates motions of the user at the input device into a resulting movement of a catheter tip, and a visualization system 12 that provides a user with real-time or near-real-time positioning information concerning the catheter tip. The system may further include closed-loop feedback using an EnSite NavX system 14 and/or optical force transducers, a robotic catheter manipulator assembly 300 (described in detail in commonly owned and copending application titled "Robotic Catheter Manipulator Assembly") for operating a robotic catheter device cartridge 400 (described in detail below and in commonly owned and copending application titled "Robotic Catheter Device Cartridge"), and manipulator support structure 150 (described in detail in commonly owned and copending application titled "Robotic Catheter System"). The system provides the user with a similar type of control provided by a conventional manual system, but allows for repeatable, precise, and dynamic movements. The respective disclosures of the above-identified and other commonly owned and copending applications discussed in this application are incorporated herein by reference.

An embodiment of robotic catheter system 10 may involve automated catheter movement. A user, such as an EP, could identify locations (potentially forming a path) on a rendered computer model of the cardiac anatomy. The system can be configured to relate those digitally selected points to positions within a patient's actual/physical anatomy, and may command and control the movement of a catheter to defined positions. Once in position, either the user or system could then perform the desired treatment or therapy—which may further be in accordance with a defined algorithm. This system could enable full robotic control by using optimized path planning routines together with closed-loop position control. Furthermore, the system could automate certain "best-practices," such as pulling the catheter across the surface, or making contact at an oblique angle.

Referring to FIG. 1, input control system 100 will be described briefly.

Input control system 100 of commonly owned and copending application titled "Robotic Catheter System Input Device," may generally allow a user to control the movement and advancement of both the catheter and sheath. Generally, several types of joysticks may be employed, including, without limitation, instrumented traditional catheter handle controls, oversized catheter models, instrumented, user-wearable gloves, and traditional joysticks. In embodiments, for example and without limitation, the joystick may be spring centering so that any movement from the center position causes an incremental movement of the actual catheter tip, or the joystick may work in absolute terms. Haptic feedback may also be incorporated to provide a user with a sense of when contact has been made.

Referring to FIG. 1, electronic control system 200 will be described briefly.

As discussed in detail in commonly owned and copending applications titled "Robotic Catheter System Input Device," and "Robotic Catheter System with Dynamic Response," many additional features may be included with embodiments of the system to, for example, improve the accuracy or effectiveness of the system. Such features may include, closed-loop feedback using EnSite NavX system 14 for creating realistic cardiac chamber geometries or models, displaying activation timing and voltage data to identify arrhythmias, and guiding precise catheter movement, and/or optical force transducers; active tensioning of "passive" steering wires to reduce the system response time; cumulative ablation while the tip is following a front-to-back ironing motion; and/or reactive/resistive impedance monitoring.

Referring to FIG. 1, visualization system 12 will be described briefly.

Visualization system 12 may provide a user with real-time or near-real-time positioning information concerning the catheter tip. In an exemplary embodiment, system 12 may include an EnSite NavX monitor 16 for displaying cardiac chamber geometries or models, displaying activation timing and voltage data to identify arrhythmias, and for facilitating guidance of catheter movement. A fluoroscopy monitor 18 may be provided for displaying a real-time x-ray image or for assisting a physician with catheter movement. Additional exemplary displays may include an ICE and EP Pruka displays, 20, 22, respectively.

Referring to FIG. 1, EnSite NavX system 14 will be described briefly.

EnSite NavX system 14 (described in detail in U.S. Pat. No. 7,263,397, titled "Method and Apparatus for Catheter Navigation and Location and Mapping in the Heart," incorporated by reference in its entirety) may be provided for creating realistic cardiac chamber geometries or models, displaying activation timing and voltage data to identify arrhythmias, and guiding precise catheter movement. EnSite NavX system 14 may collect electrical data from catheters and use this information to track or navigate their movement and construct three-dimensional (3-D) models of the chamber.

Referring to FIGS. 1 and 3a-5e, the catheter and sheath configuration of robotic catheter manipulator assembly 300 and robotic catheter device cartridges 400 will be described in detail for facilitating an understanding of robotic catheter system 10, and robotic catheter rotatable device cartridge 700 and its related components.

Figure 2:
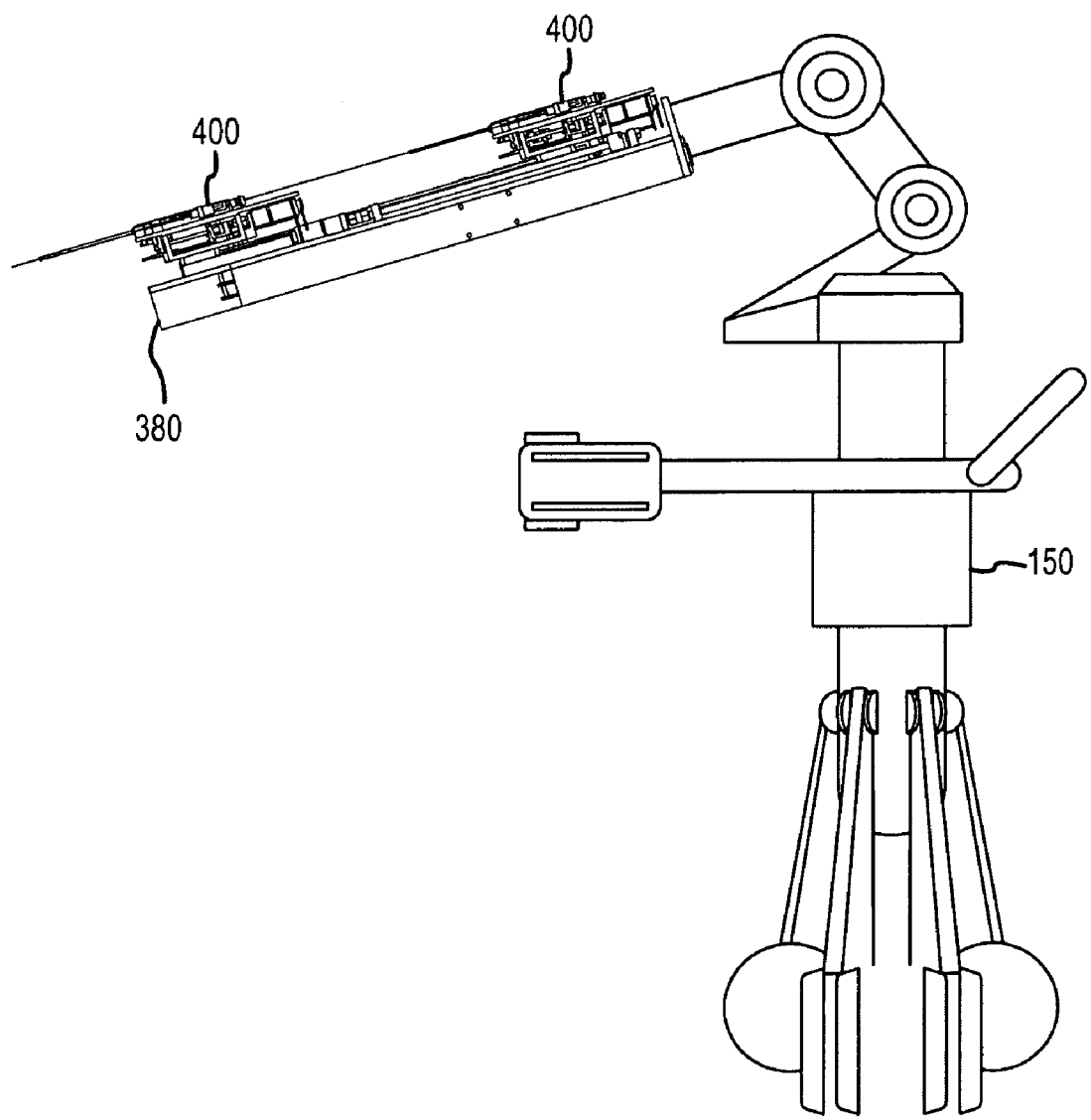
FIG. 2 is an isometric diagrammatic view of a first embodiment of a robotic catheter manipulator support structure, illustrating a robotic catheter manipulator slightly angled from a generally horizontal position.

As generally shown in FIGS. 1 and 3a-5e, robotic catheter system 10 may include one or more robotic catheter manipulator assemblies 300 that serve as the mechanical control for the movements or actions of one or more robotic catheter device cartridges 400. FIG. 1 illustrates a generally vertically oriented manipulator assembly 300 for minimizing approach angle, and FIG. 2 illustrates a manipulator assembly 380 slightly angled from a generally horizontal position. A first embodiment of manipulator assembly 302 may respectively include both catheter and sheath manipulator mechanisms 304, 306. In this arrangement, the catheter and sheath manipulator mechanisms 304, 306 may be aligned such that the catheter can pass through the sheath in a coaxial arrangement. Each mechanism 304, 306 may be further capable of independent advancement/retraction (shown generally as directions $D_1$ and $D_2$) and independent four-wire steering control (e.g., eight total steering wires, comprising four sheath control wires and four catheter control wires), as discussed in detail below.

With a configuration of robotic catheter system 10, such as shown in FIGS. 1 and 3a-5e, there will be relative travel of a first embodiment of catheter and sheath cartridges 402, 404 and relative movement associated with a portion of a catheter 406 between the two cartridges 402, 404. For many embodiments, there may be a water-tight fit of a proximal sheath opening 408, which can sometimes create resistance to catheter advancement. In order to help eliminate/reduce the potential issue of columnar buckling of catheter 406, a length of stiff material, such as, for example, a solid metal rod or fiber reinforced composite, may be incorporated on the interior of the proximal portion of catheter 406. Such a material may locally increase the catheter's bending stiffness and provide enhanced buckling support. Thus catheter 406 may be proximally stiffened so that the length of the catheter proximally extending from sheath cartridge 404 is less likely to buckle during relative translation, as the entire length of catheter 406 extends into sheath 410.

Referring to FIGS. 1 and 3a-5e, the first embodiment of robotic catheter manipulator assembly 302 will be described in detail.

Figure 3A:
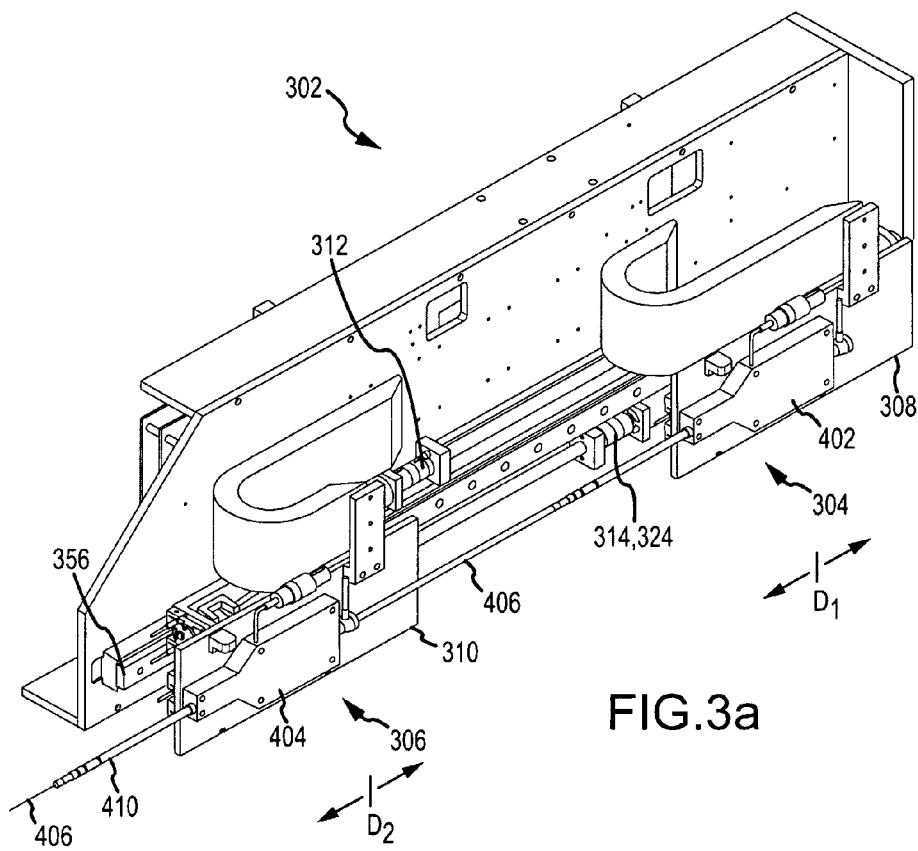
FIGS. 3a-3c are enlarged isometric.
Figure 3B:
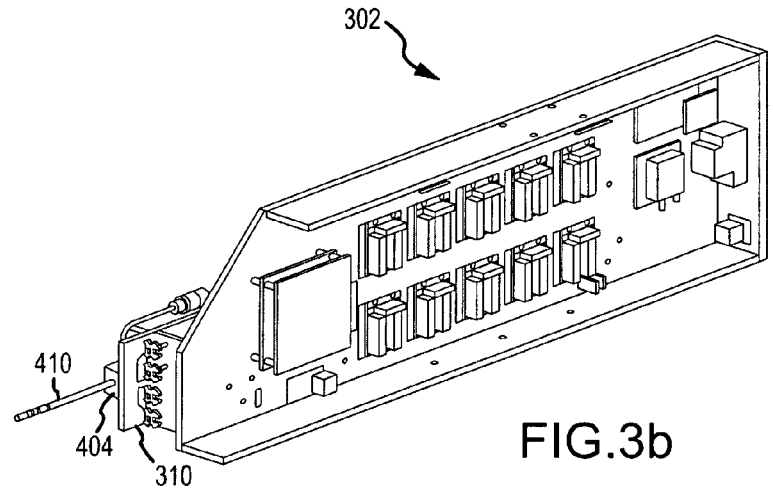
Figure 3C:
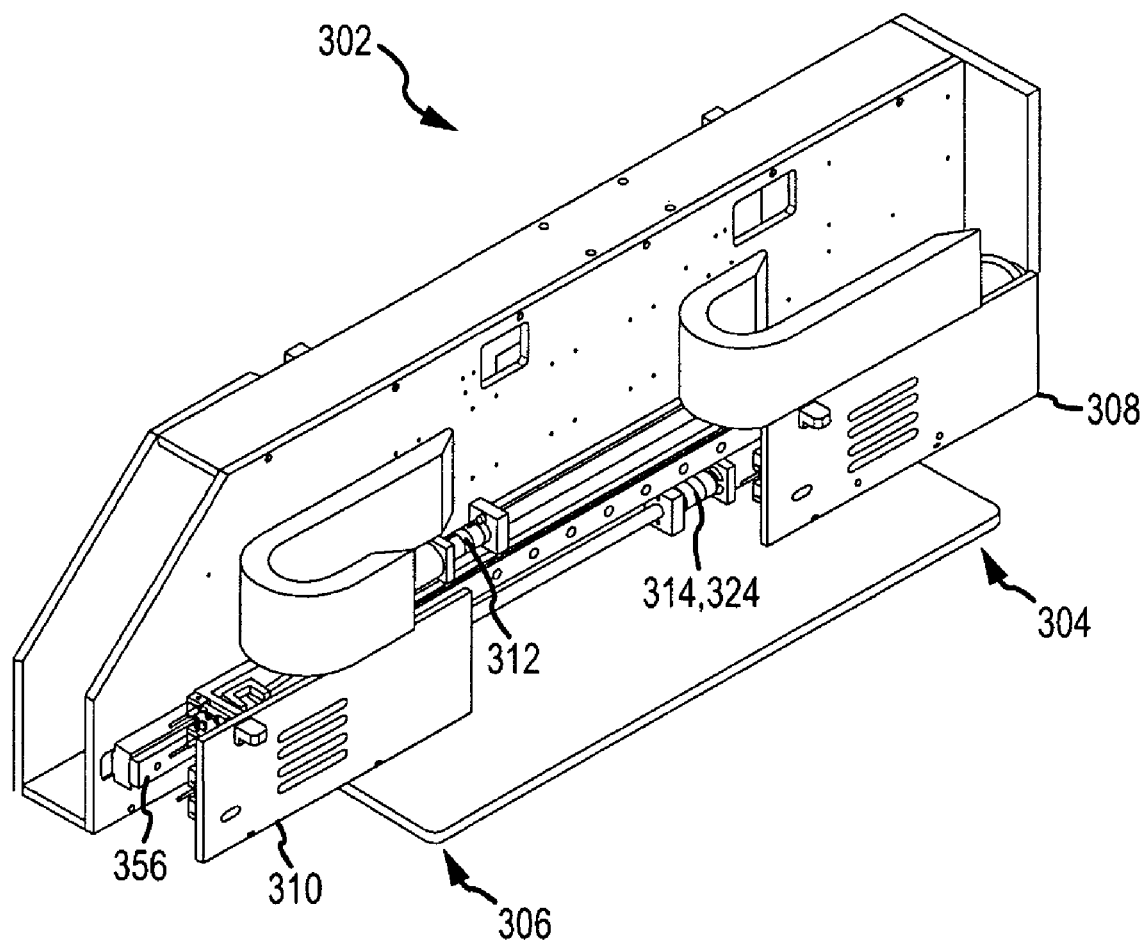
Figure 3H:
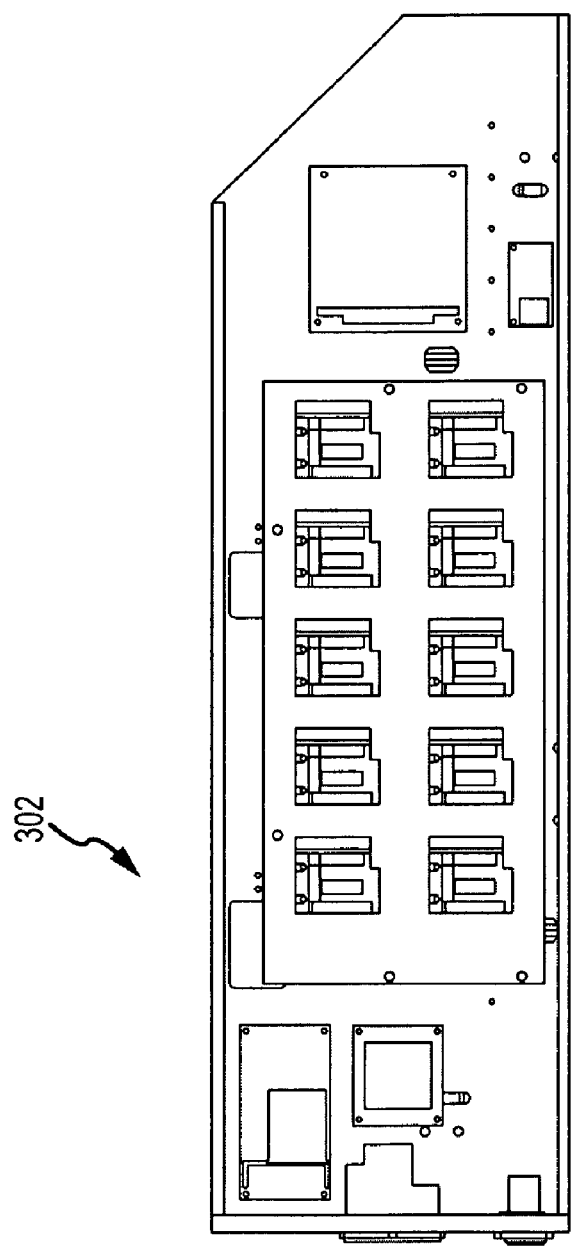
Figure 3I:
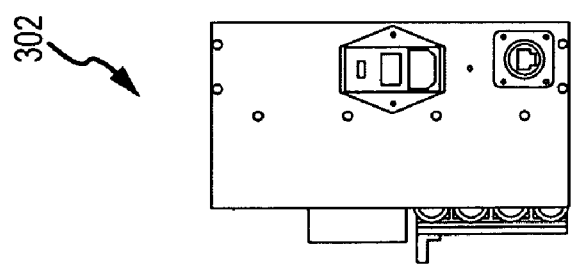

As generally shown in FIGS. 1 and 3a-5e, robotic catheter system 10 which includes one or more robotic catheter manipulator assemblies 300, includes the first embodiment of robotic catheter manipulator assembly 302 including both catheter and sheath manipulation mechanisms 304, 306 for manipulating, for example, catheter and sheath cartridges 402, 404. Manipulator assembly 302 may include interconnected/interlocking manipulation bases 308, 310 for catheter and sheath cartridges 402, 404, and likewise may include electrical "handshake" functionality as discussed below. Each interlocking base 308, 310 may be capable of travel in the longitudinal direction of the catheter/sheath ($D_1$, $D_2$ respectively). In an embodiment, $D_1$ and $D_2$ may each represent a translation of approximately 8 linear inches. As shown in FIG. 3a, each interlocking base may be translated by high precision drive mechanisms 312, 314. Such drive mechanisms may include, for example and without limitation, a motor driven lead screw or ball screw.

Figure 4A:
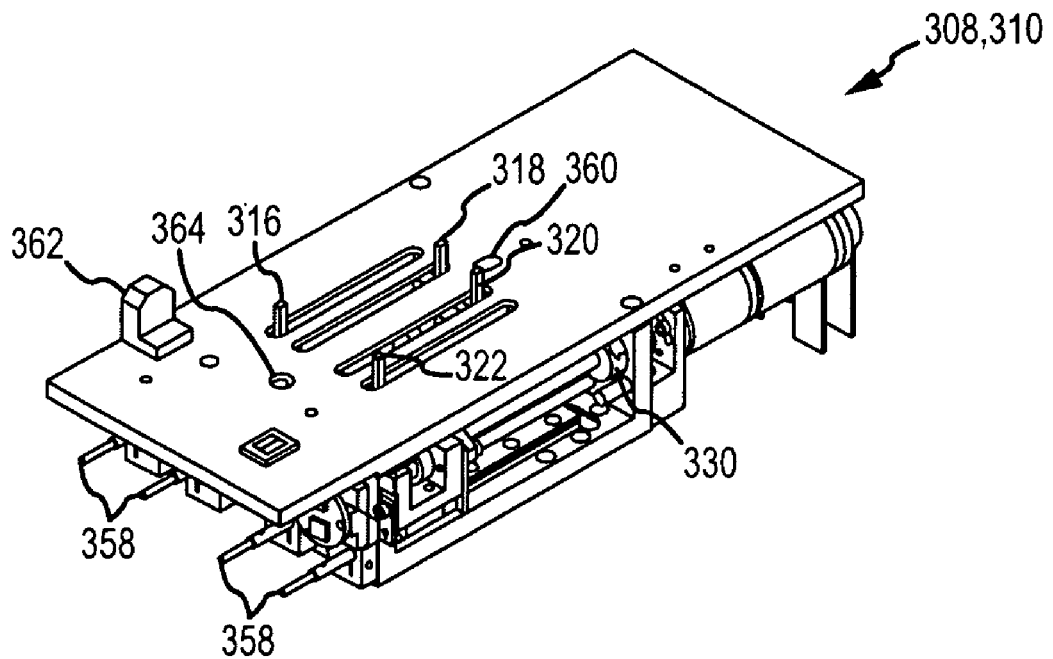
FIGS. 4a-4c are enlarged isometric views.
Figure 4B:
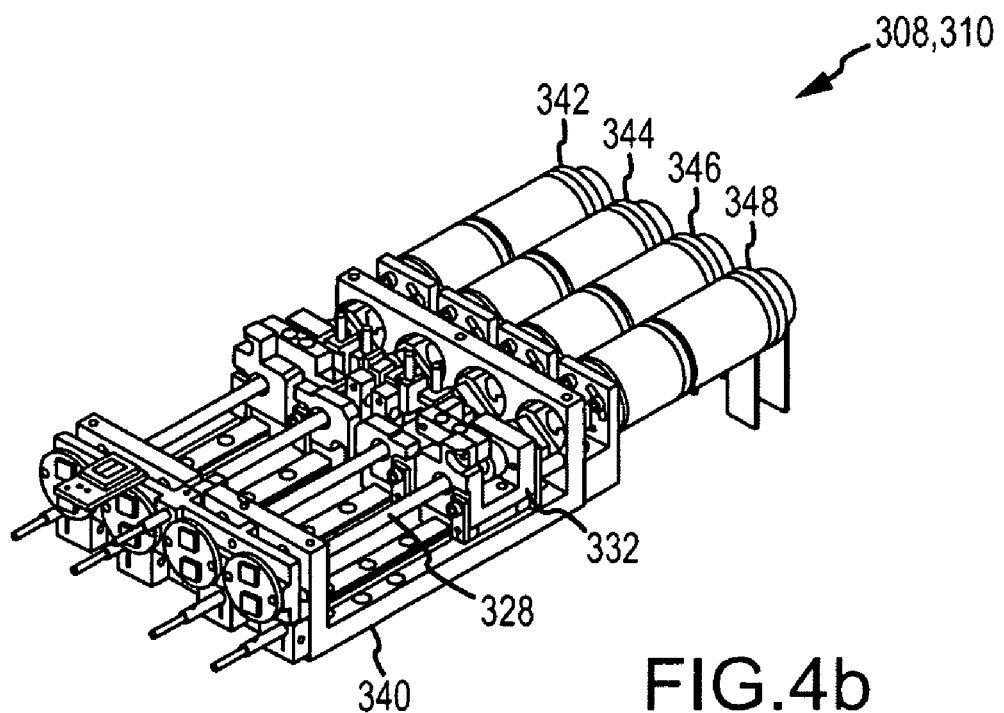
Figure 4C:
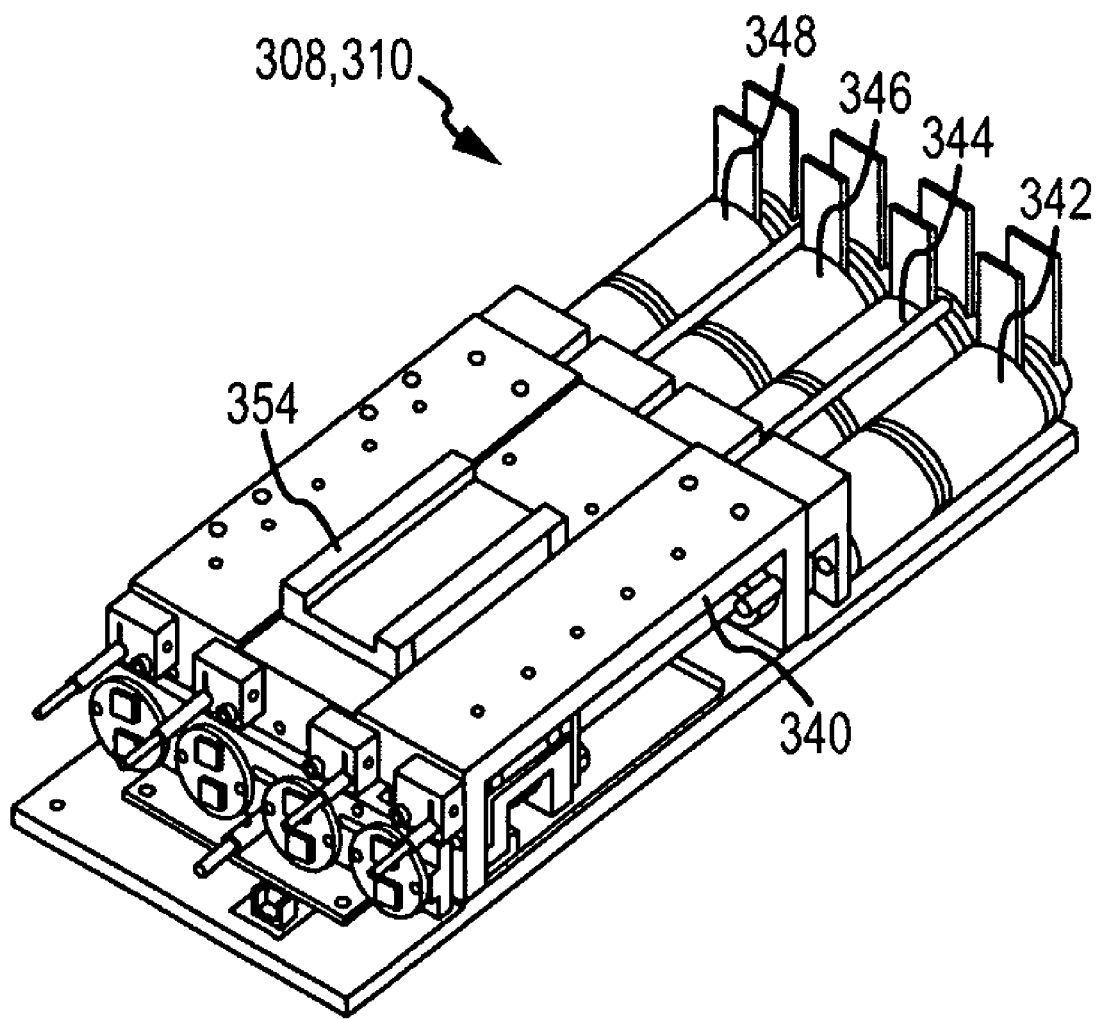
Figure 4D:
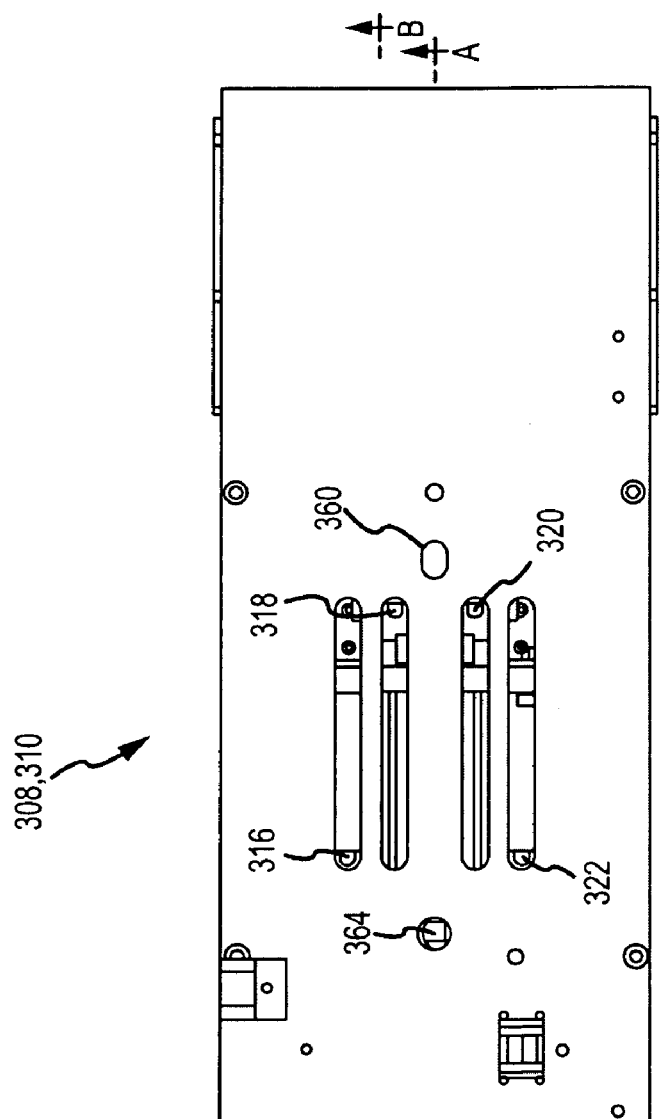
Figure 4E:
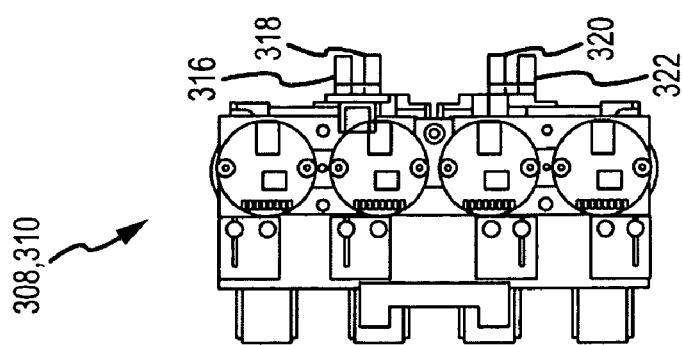

As shown in FIGS. 3a-3i and 4a-4g, for each cartridge 402, 404, an associated manipulation base 308, 310 may include a plurality of fingers 316, 318, 320 and 322, (e.g., one per steering wire) that extend or protrude upwardly to contact and interact with the steering wire slider blocks (such as slider blocks 412, 414, 416, 418) to independently tension select steering wires 420, 422, 424, 426. Each finger can be configured to be independently actuated by a precision drive mechanism, such as a motor driven ball screw 324, and may be outfitted with force sensors to measure corresponding steering wire tension. Each motor driven ball screw (for both finger control and cartridge translation control) may further include encoders to measure a relative and/or an absolute position of each element of the system. As shown in FIG. 4a, bearing 332 and coupler 330 of ball screw 324 may engage frame 340 of respective bases 308, 310 and a corresponding finger 316, 318, 320 or 322 may be mounted adjacent a strain gauge for measuring the corresponding steering wire tension.

Referring to FIGS. 4a-4g, bases 308, 310 may include exemplary components such as motors 342, 344, 346 and 348, respectively coupled to fingers 316, 318, 320 and 322. A bearing 354 may be provided for sliding of bases 308, 310 on track 356. A plurality of inductive sensors (e.g. home sensors) 358 may be provided for guiding each manipulation base to a safe position.

Manipulator assembly 302 may be disposed in a vertical configuration (see FIG. 1) for minimizing both the approach angle of the catheter and the distance the catheter must extend from the patient, or slightly angled from a generally horizontal position (see FIG. 2). In the vertical configuration of FIG. 1, the approach angle and catheter extension distance may be minimized by vertically orienting the backplane of the manipulator head, with the interlocking cartridges positioned at the lower extreme such that they may travel nearly horizontally and substantially in line with the point of entry into the patient (e.g., as generally illustrated in FIG. 1). In such an embodiment, with the backplane of the manipulator head vertically oriented, the positioning of the manipulator head structure may allow the proximal control of the catheter/sheath to be held closely to the patient's body without substantial structural interference. In an embodiment, high-precision drive mechanisms 312, 314 for translating each of the catheter and sheath cartridges 402, 404 may be positioned generally below the manipulator bases 308, 310 to allow the respective cartridges to be positioned toward the lower area of the manipulator. By holding a close distance, the ingress angle of the catheter/sheath may be minimized, and the manipulator control may be positioned more closely to an insertion site.

Referring to FIGS. 1-3m, particularly FIGS. 3j-3m, robotic catheter manipulator assembly 302 may be usable with a robotic catheter rotatable device cartridge 700, described in detail below. As shown in FIG. 3m, manipulator base 308 may be replaced with a robotic catheter rotatable drive mechanism 500, described briefly herein and in detail in commonly owned and copending application titled "Robotic Catheter Rotatable Drive Mechanism," and a robotic catheter rotatable drive head 600.

Referring to FIGS. 1 and 5a-5e, catheter and sheath cartridges 402, 404 will be described in detail.

As briefly discussed above, robotic catheter system 10 may include one or more cartridges 400, with manipulator 302 including at least two cartridges 402, 404, each of which may be respectively designed to control the distal movement of either the catheter or the sheath. With respect to catheter cartridge 402, catheter 406 may be substantially connected or affixed to cartridge 402, so that advancement of cartridge 402 correspondingly advances catheter 406, and retraction of the cartridge retracts the catheter. As further shown in FIGS. 5a-5e and discussed above, in an embodiment, each cartridge 402, 404 may include slider blocks (e.g., 412, 414, 416, 418), each rigidly (and independently) connected or affixed to one of a plurality of catheter steering wires (e.g., 420, 422, 424, 426) in a manner that permits independent tensioning of each steering wire. The cartridge may be provided as a disposable item that is capable of being easily positioned (e.g., snapped) into place in an overall assembly. In an embodiment, as discussed in detail below, the cartridge may include an electrical "handshake" device or component to allow the system to properly identify the cartridge (e.g., by type and/or proper placement/positioning). Sheath cartridge 404 may be designed in a similar manner as the catheter cartridge 402, but will typically be configured to provide for the passage of catheter 406. Assembly 302 may include a plurality (e.g., as many as ten or more) of independent driving mechanisms (e.g. motor driven ball screws 324).

For some embodiments, the catheter and sheath cartridge can be designed to be substantially similar, and in that context a reference to either may relate to both. For example, as shown in FIGS. 5a-5e, the design of the catheter/sheath cartridge may include upper and lower cartridge sections 428, 430, and independent slider blocks 412, 414, 416, 418. The system is not generally limited to specific material selection or formation techniques. However, in an embodiment, the upper and lower cartridge sections 428, 430 may be injection molded using a polycarbonate material. Each slider block 412, 414, 416, 418 may be connected to a separate catheter steering wire 420, 422, 424, 426, and may be formed of a Teflon-like material such as, for example, Delrin AF. When in contact with the cartridge housing portions 428, 430, such Teflon-like slider blocks may maintain a low static and dynamic coefficient of friction and may avoid the need for additional lubrication.

Figure 5A:
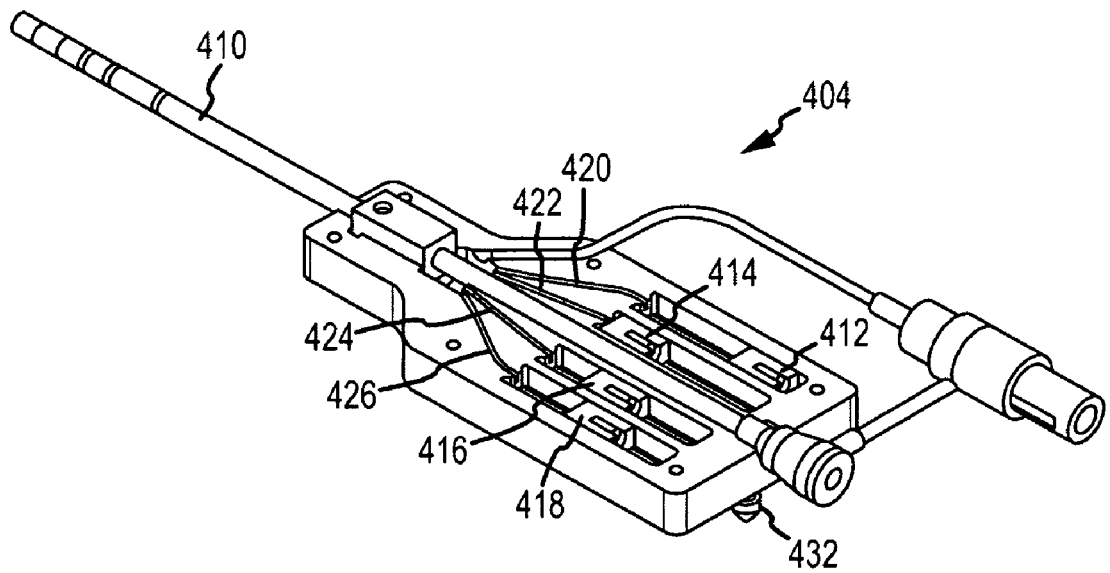
FIGS. 5a-5e are enlarged isometric views of a first embodiment of a robotic catheter device cartridge, with FIG. 3a illustrating an exemplary usage of the robotic catheter device cartridge.
Figure 5B:
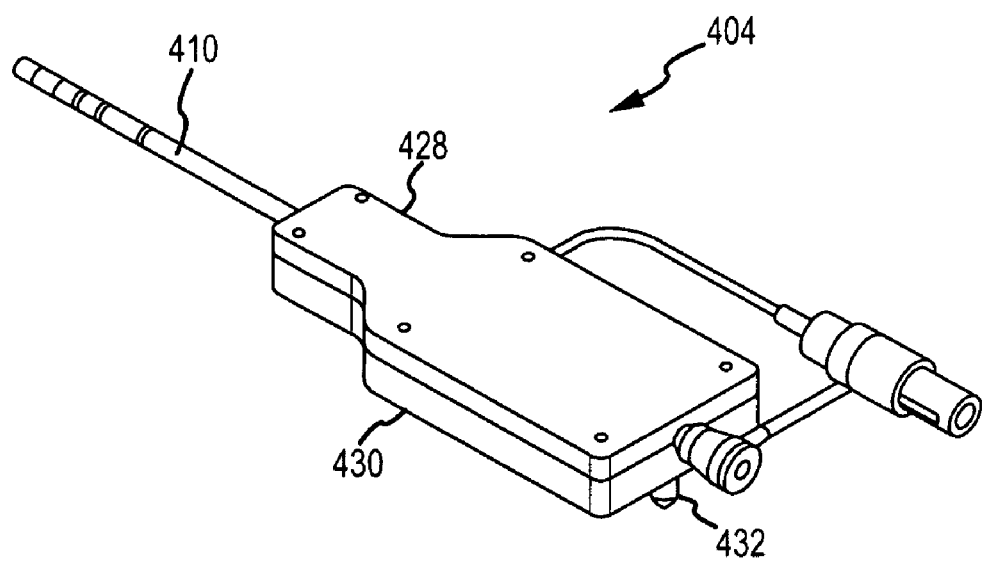
Figure 5C:
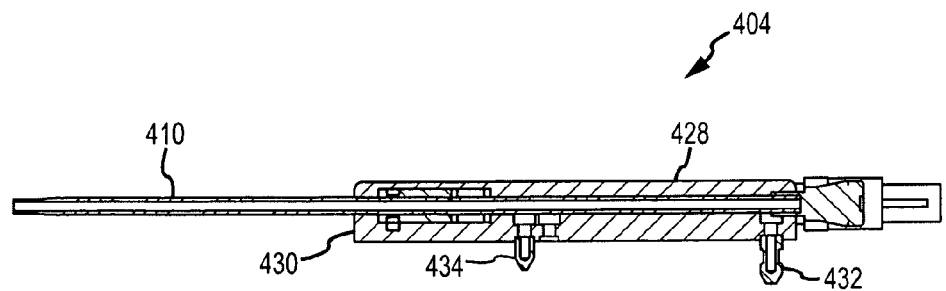
Figure 5D:
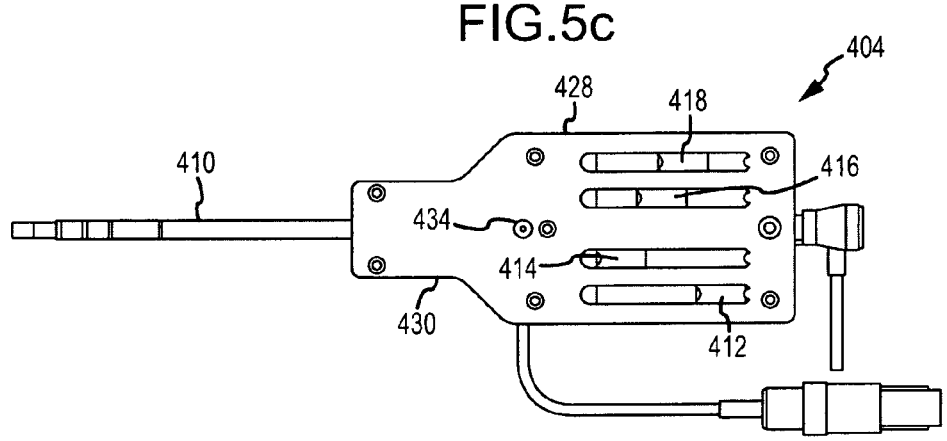
Figure 5E:
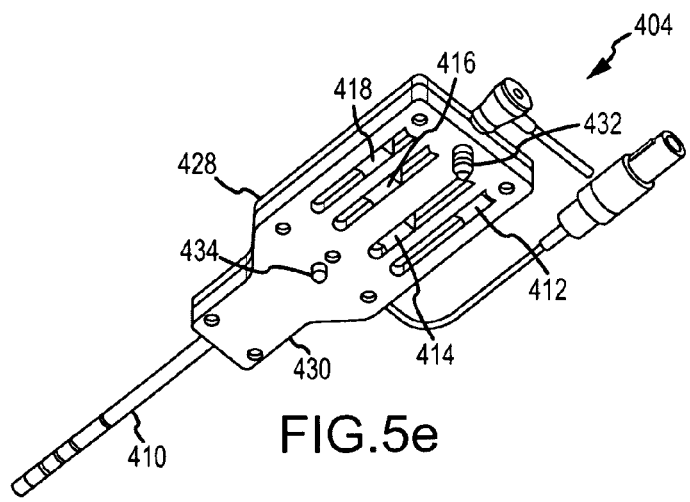

Referring to FIGS. 3a-5e and as discussed above, catheter and sheath cartridges 402, 404 may be configured to secure or lock down onto respective interconnecting catheter and sheath manipulation bases 308, 310. To couple cartridge 402 (and 404) with base 308 (and 310), one or more locking pins (e.g., 432 in FIGS. 5a, 5d and 5e) on the cartridge may engage one or more mating recesses 360 in the base (see FIG. 4a). In an embodiment, such recesses 360 may include an interference lock such as a spring detent or other locking means. In an embodiment, such other locking means may include a physical interference that may require affirmative/positive action by the user to release the cartridge. Such action may include or require actuation of a release lever 362. Additionally, as shown in FIGS. 5c, 5d and 5e, cartridge 402 (and 404) may include one or more locator pins 434 that are configured to passively fit into mating holes on the base (e.g., 364 in FIG. 4a).

In an embodiment, a user (e.g. an EP) may first manually position catheter 406 and sheath 410 (with catheter 406 inserted in sheath 410) within the vasculature of a patient. Once the devices are roughly positioned in relation to the heart, the user may then engage or connect (e.g., "snap-in") the catheter cartridge into place on interconnecting/interlocking bases 308, 310 of manipulator assembly 302, for example, by inserting the locking/locating pins 432, 434 of the cartridges into mating holes 360, 364 of respective base 308, 310. When the cartridge is interconnected with the base, each of the plurality of fingers 316, 318, 320 or 322 may fit into recesses formed between the distal edge of slider blocks 412, 414, 416, 418 and a lower portion of the cartridge housing. Such recesses are shown in, for example, FIGS. 5d and 5e.

Each finger may be designed to be actuated in a proximal direction to correspondingly push each respective slider block. The slider block can be configured to force the finger to self center on its geometry when contact is first made. Such a centering feature may be facilitated by the contact surface of the slider block. For example, as shown in FIGS. 5d and 5e, the slider block may include an engagement surface (e.g., shaped as a semi-cylindrical recess in the forward facing portion). This surface may be configured to mate or communicate with a matching round portion of a corresponding finger.

With sufficiently rigid coupling between each slider block and a corresponding steering wire, pushing a slider block in a proximal direction may cause an attached steering wire to tension and thus laterally deflect the distal end of the catheter and sheath 406, 410. Moreover, in such an embodiment, because there is no rigid connection between each finger and its associated slider block, the manipulator assembly 302 cannot pull the steering wire in a forward direction. That is, when each block is actuated, it is only possible to tension the steering wire. Furthermore, because the push-actuation of each slider block occurs near that block's bottom surface, a moment may be imposed on the block. Because such a moment may increase the likelihood of the block binding during travel, the length of the block may be optimized to reduce or minimize contact forces between the block and the cartridge housing.

Referring to FIGS. 1-8d, particularly FIGS. 6a-8d, robotic catheter rotatable device cartridge 700 usable with robotic catheter manipulator assembly 302 will be described in detail in conjunction with robotic catheter rotatable drive mechanism 500 (described in detail in commonly owned and copending application titled "Robotic Catheter Rotatable Drive Mechanism.") and robotic catheter rotatable drive head 600.

As briefly discussed above, robotic catheter system 10 may include one or more cartridges 400, with manipulator 302 including at least two cartridges 402, 404, each of which may be respectively designed to control the distal movement of either the catheter or the sheath. As shown in FIGS. 3a and 6a-8d, catheter manipulation base 308 and catheter cartridge 402 may be respectively replaced with robotic catheter rotatable drive mechanism 500 and robotic catheter rotatable drive head 600, and robotic catheter rotatable device cartridge 700.

Figure 6A:
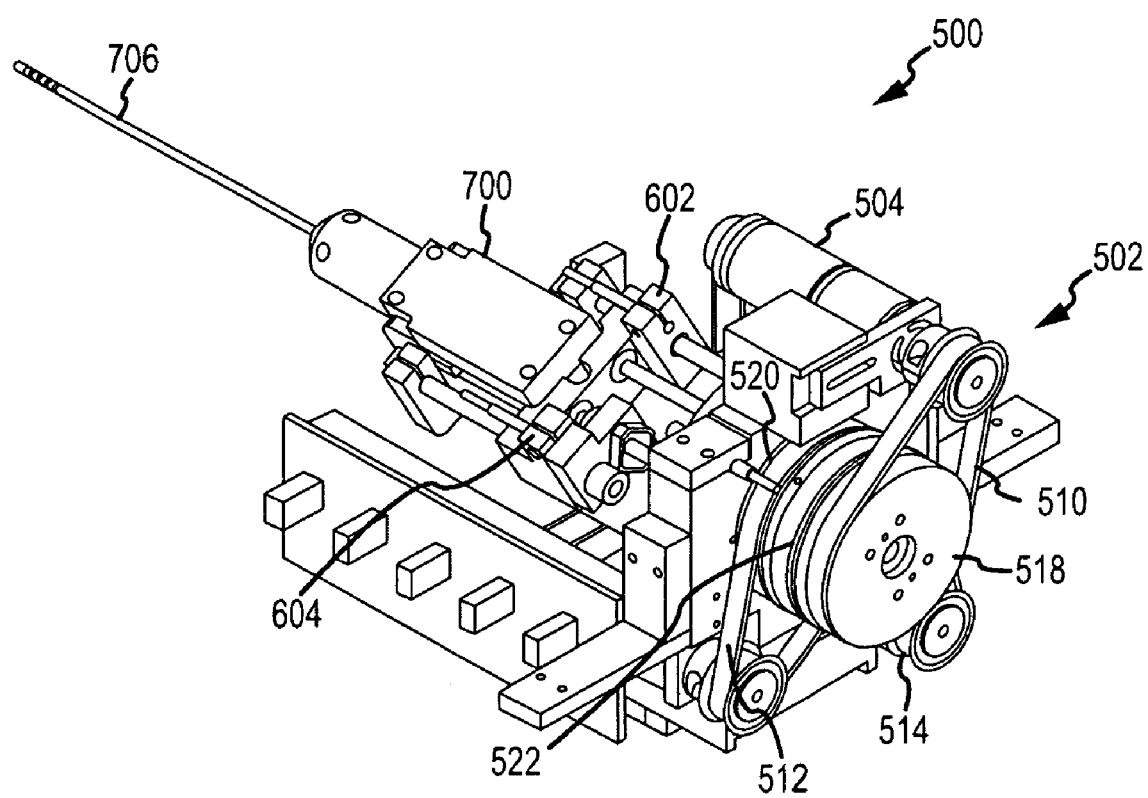
FIGS. 6a-6c are enlarged isometric.
Figure 6B:
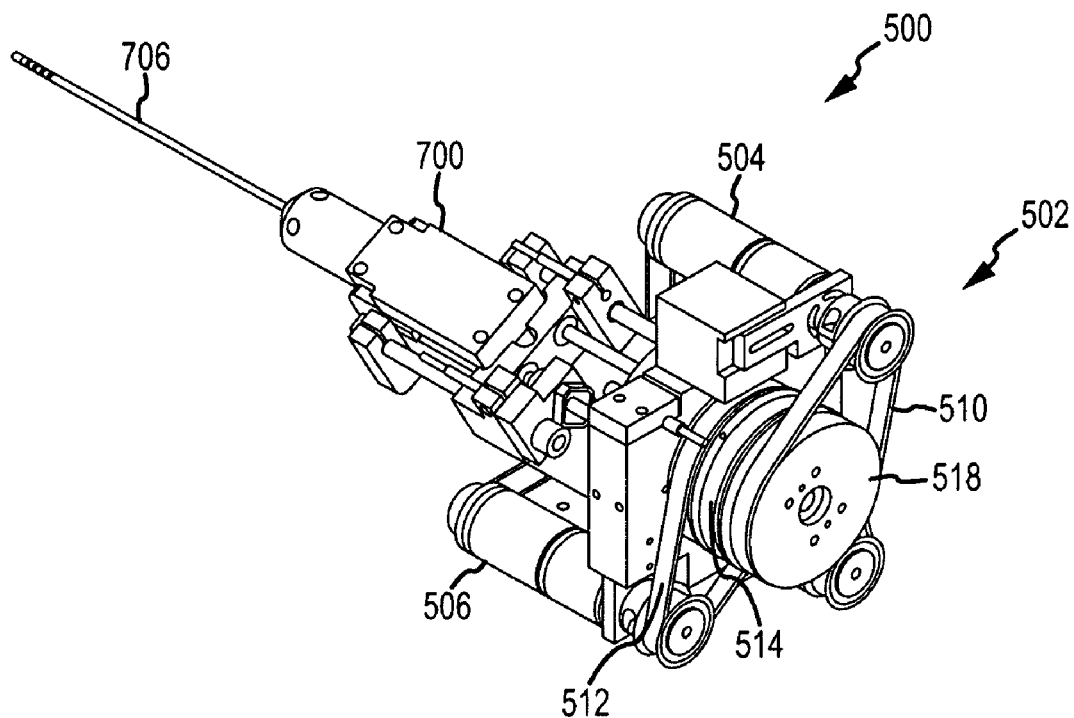
Figure 6C:
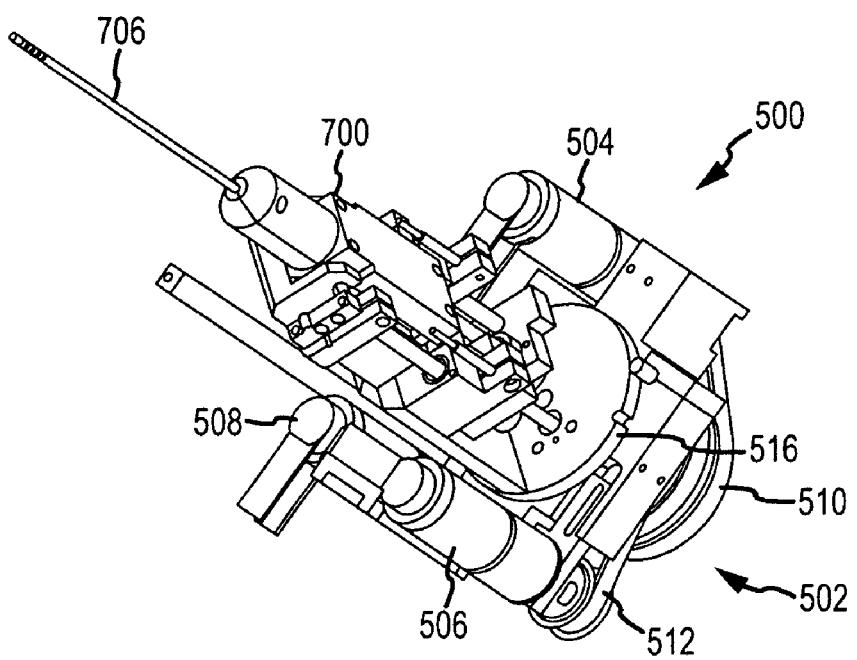
Figure 6D:
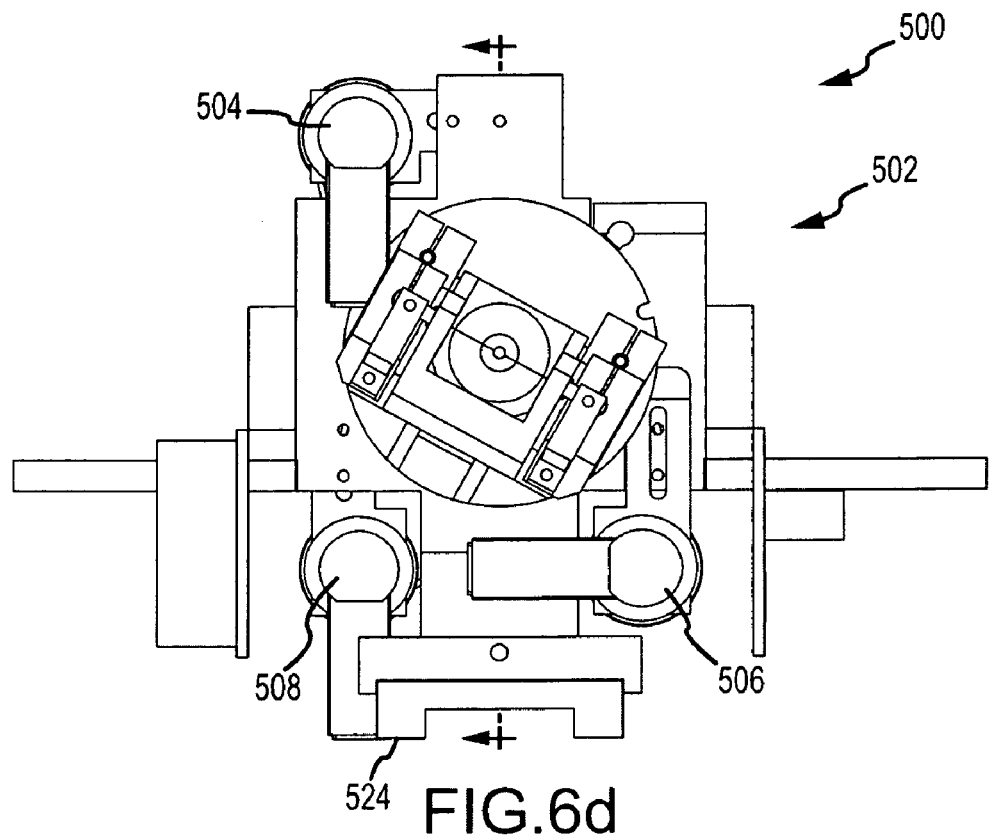
FIGS. 6d and 6e are left side and right side.
Figure 6E:
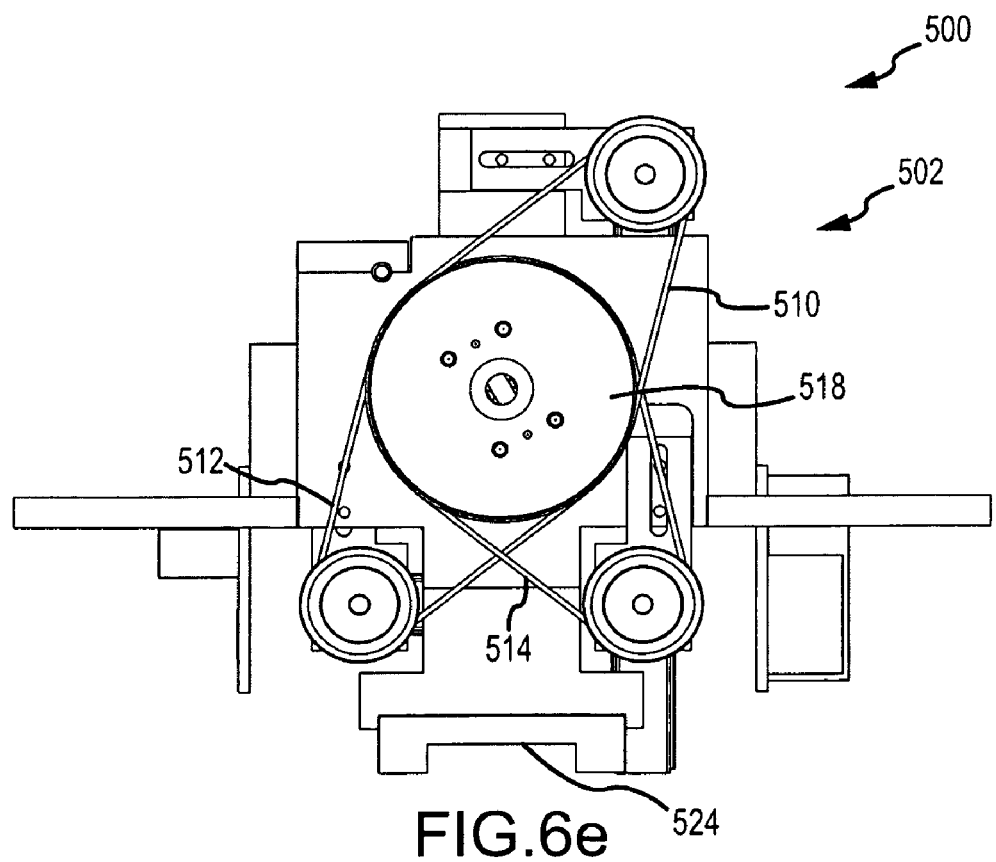
Figure 6F:
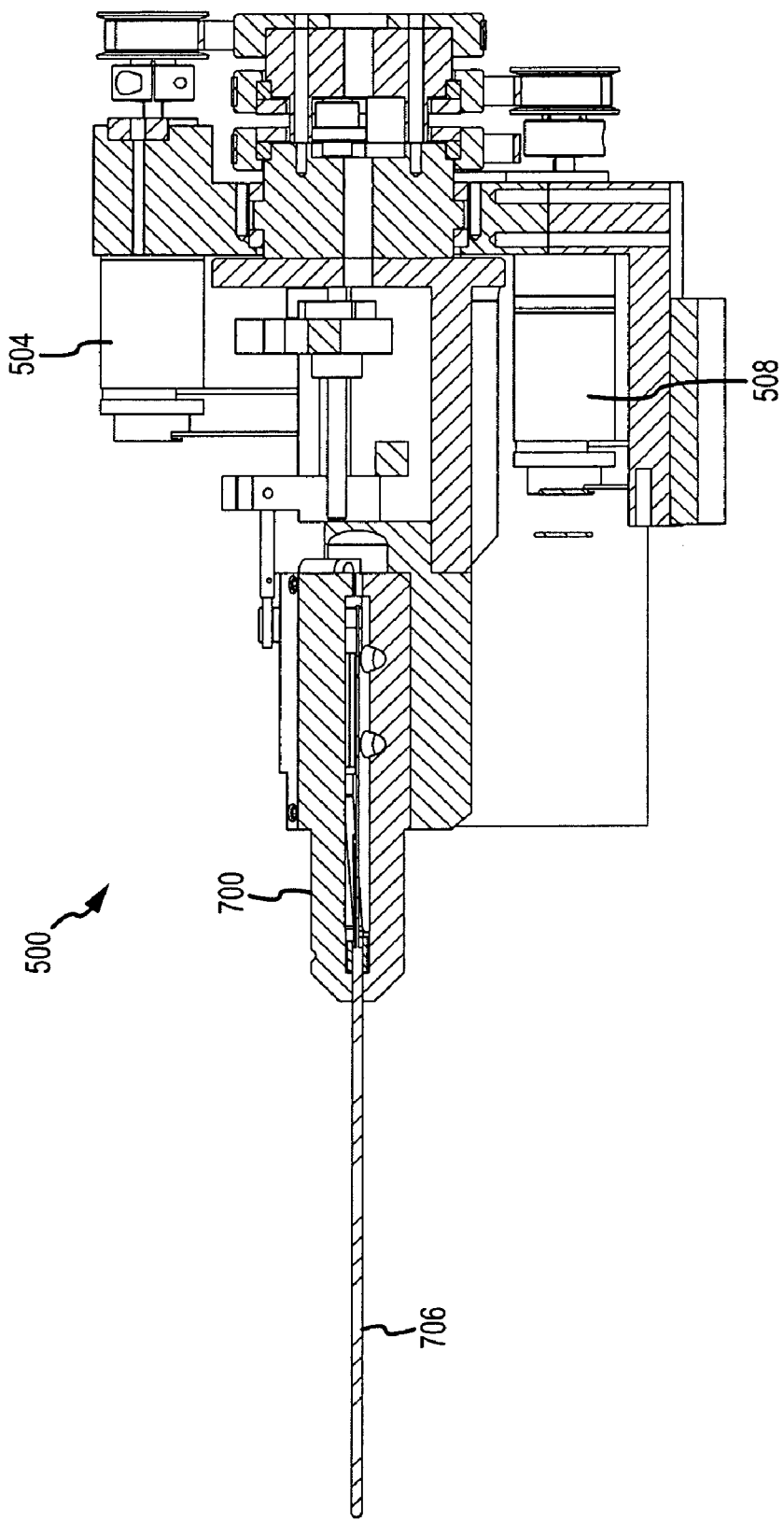
FIG. 6f is section A-A taken generally along line A-A in FIG. 6d, views of a robotic catheter rotatable drive mechanism, with FIGS. 3j-3m illustrating an exemplary usage of the robotic catheter rotatable drive mechanism.

Referring to FIGS. 6a-6f, mechanism 500 may generally include a motor and belt drive assembly 502 for rotatably driving robotic catheter rotatable drive head 600 including cartridge 700 releasably mounted thereon. Assembly 502 may include motors 504, 506, 508 for respectively driving belts 510, 512, 514. While belt 510 may rotatably drive the shaft of drive head mount 516 via pulley/gear 518 to rotatably drive robotic catheter rotatable drive head 600, belts 512, 514 may drive pulleys/gears 520, 522 to move right and left wire sliders 602, 604 of drive head 600 along the axis of cartridge 700 (see also FIGS. 7h-7n, which illustrate the respective drive configuration for pulleys/gears 518, 520 and 522). As shown in FIG. 6d, a bearing 524 may be provided for slidable positioning of mechanism 500 on track 356 of manipulator 302.

Figure 7A:
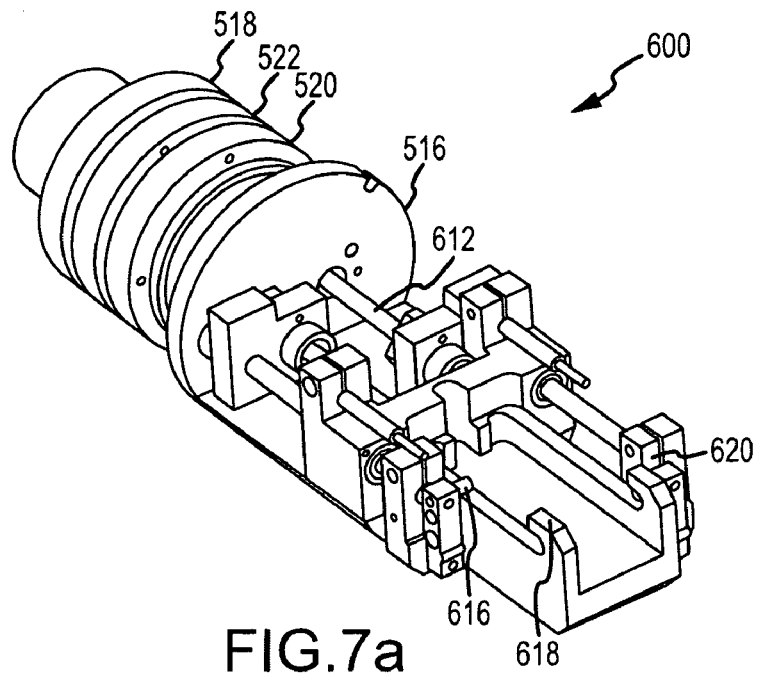
FIGS. 7a and 7b are enlarged isometric.
Figure 7B:
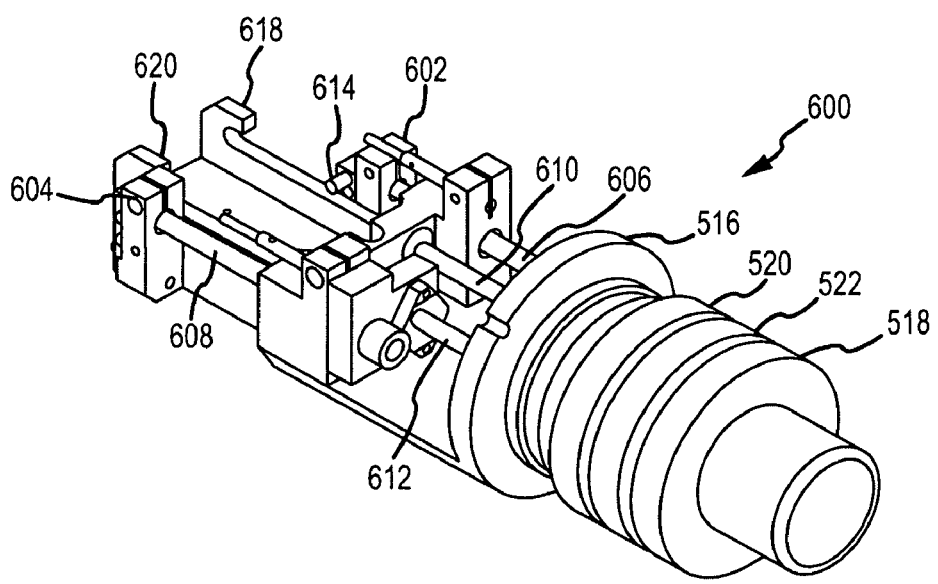
Figure 8A:
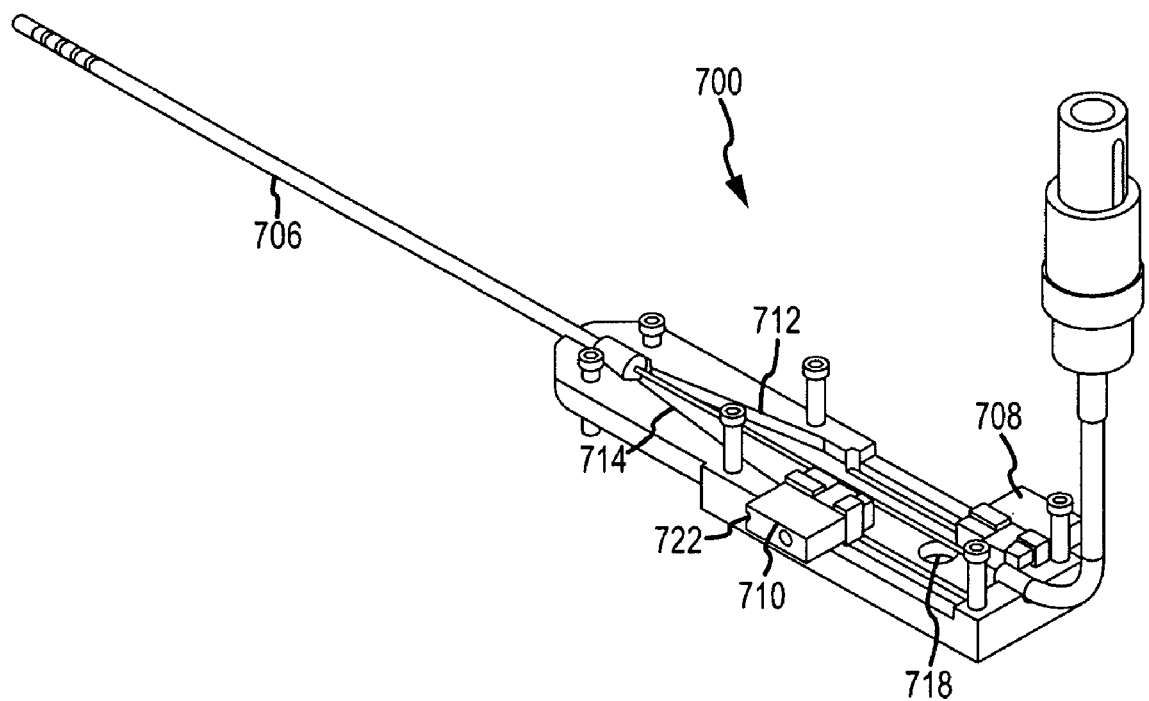

Referring to FIGS. 7a-7n, robotic catheter rotatable drive head 600 may generally include sliders 602, 604 as discussed above respectively mounted to rods 606, 608, and driven by lead screws 610, 612. Lead screws 610, 612 may be respectively driven by pulleys/gears 520, 522, and drive head 600 may include detents 614, 616 for driving engagement with slider blocks 708, 710 of cartridge 700. A pair of hooks 618, 620 may also be provided for retention of cartridge 700.

Referring to FIGS. 7a-8d, cartridge 700 may include catheter 706 substantially connected or affixed thereto, so that advancement or rotation of cartridge 700 correspondingly advances or rotates catheter 706, and retraction of the cartridge retracts the catheter. Slider blocks 708, 710 may each be rigidly (and independently) connected or affixed to one of a plurality of catheter steering wires 712, 714 in a manner that permits independent tensioning of each steering wire. Steering wires 712, 714 may be connected to the slider blocks by means of set screws 716 or other means known in the art. A pair of magnetic mounts 718 may be provided for complementary engagement with drive head 600. Further, slider blocks 708, 710 may include concave indents 720, 722 for complementary engagement with detents 614, 616 of drive head 600. Hooks 618, 620 of drive head 600 may also engage with slider blocks 708, 710 as shown in FIG. 7d. The cartridge may be provided as a disposable item that is capable of being easily positioned (e.g., snapped) into place in an overall assembly. In an embodiment, as discussed in detail below, the cartridge may include an electrical "handshake" device or component to allow the system to properly identify the cartridge (e.g., by type and/or proper placement/positioning). Assembly 302 may include a plurality (e.g., as many as ten or more) of independent driving mechanisms (e.g. motor driven ball screws 324).

As shown in FIGS. 8a-8d, the design of cartridge 700 may include upper and lower cartridge sections 724, 726, and independent slider blocks 708, 710. The system is not generally limited to specific material selection or formation techniques. However, in an embodiment, the upper and lower cartridge sections 724, 726 may be injection molded using a polycarbonate material. Each slider block 708, 710 may be connected to a separate catheter steering wire 712, 714, and may be formed of a Teflon-like material such as, for example, Delrin AF. When in contact with the cartridge housing portions 724, 726, such Teflon-like slider blocks may maintain a low static and dynamic coefficient of friction and may thus avoid the need for additional lubrication.

Referring to FIGS. 1-8d and as discussed above, catheter and sheath cartridges 700, 404 may be configured to secure or lock down onto respective interconnecting catheter drive mechanism 500 and drive head 600, and sheath manipulation base 310. In an embodiment, a user (e.g. an EP) may first manually position catheter 706 and sheath 410 (with catheter 706 inserted in sheath 410) within the vasculature of a patient. Once the devices are roughly positioned in relation to the heart, the user may then engage or connect (e.g., "snap-in") the catheter and sheath cartridges into place on drive mechanism 500 and drive head 600, and sheath manipulation base 310 of manipulator assembly 302, for example. When the cartridges are interconnected with the base, for sheath cartridge 404 each of the plurality of fingers 316, 318, 320 or 322 may fit into recesses formed between the distal edge of slider blocks 412, 414, 416, 418 and a lower portion of the cartridge housing. For catheter cartridge 700, detents 614, 616 may engage slider blocks 708, 710 as discussed above.

Each finger/detent may be designed to be actuated in a proximal direction to correspondingly push each respective slider block. The slider block can be configured to force the finger to self center on its geometry when contact is first made. Such a centering feature may be facilitated by the contact surface of the slider block.

With sufficiently rigid coupling between each slider block and a corresponding steering wire, pushing a slider block in a proximal direction may cause an attached steering wire to tension and thus laterally deflect the distal end of the catheter and sheath 706, 410. For rotation of catheter 706, cartridge 700 may be rotated as needed by pulley/gear 518. Since cartridge 700 is also allowed to spin infinitely, this further amplifies the maneuverability of catheter 706. Moreover, in such an embodiment, because there is no rigid connection between each finger/detent and its associated slider block, the manipulator assembly 302 or drive mechanism 500 and drive head 600 cannot pull the steering wire in a forward direction. That is, when each block is actuated, it is only possible to tension the steering wire.

Referring to FIGS. 9a-11b, embodiments of manipulation bases and cartridges described in detail in commonly owned and copending applications titled "Robotic Catheter Manipulator Assembly" and "Robotic Catheter Device Cartridge" are illustrated.

Figure 9A:
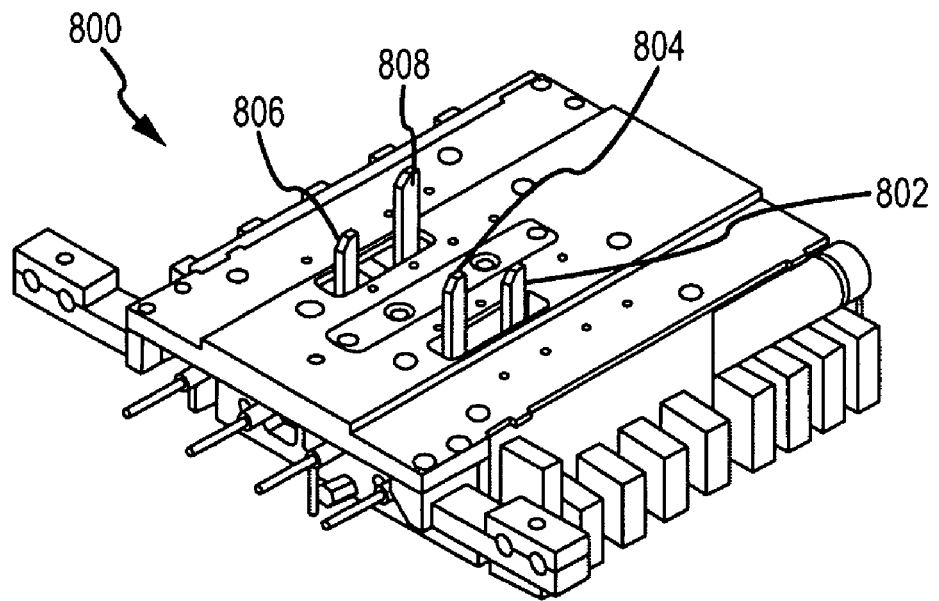
FIGS. 9a and 9b are enlarged isometric views of a second embodiment of a robotic catheter manipulation base and robotic catheter device cartridge.
Figure 9B:
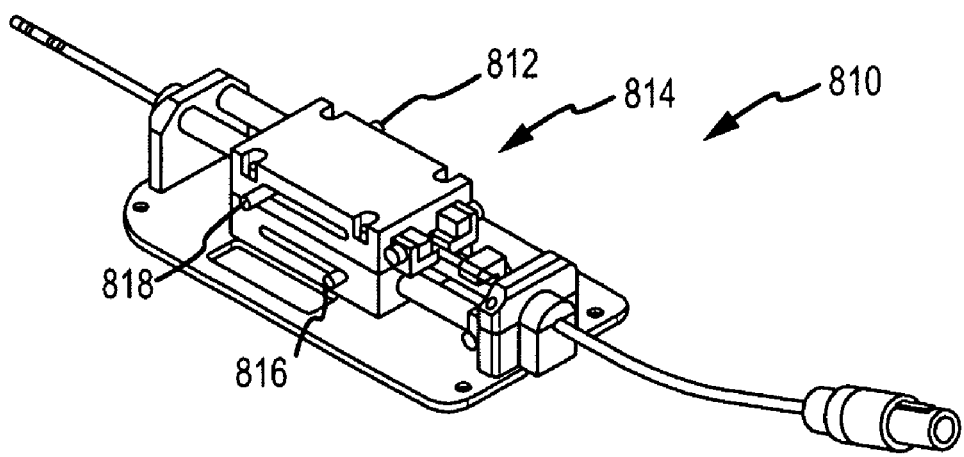

Referring to FIGS. 9a and 9b, a manipulation base 800 includes protruding and linearly movable fingers 802, 804, 806, 808 for operating cartridge 810 including pins 812, 814 (opposite of pin 816), 816 and 818. It is conceivable that for the design of mechanism 500 and cartridge drive head 600 discussed above, slider blocks 708, 710 of cartridge 700 may be linearly movable by a mechanism similar to manipulation base 800.

Figure 10A:
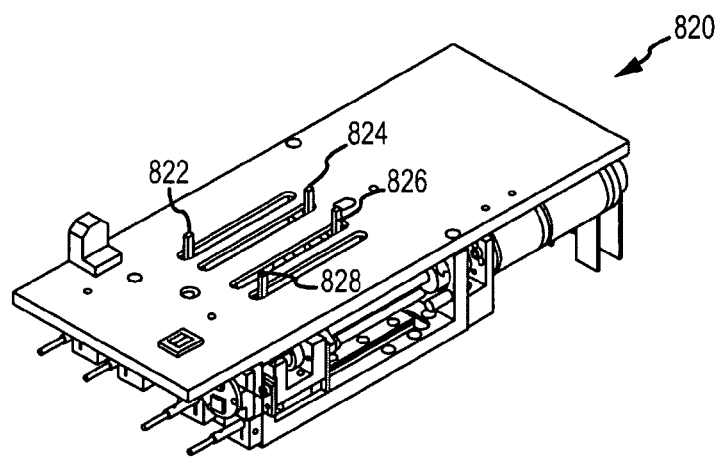
FIGS. 10a and 10b are enlarged isometric and bottom views of a third embodiment of a robotic catheter manipulation base and robotic catheter device cartridge.
Figure 10B:
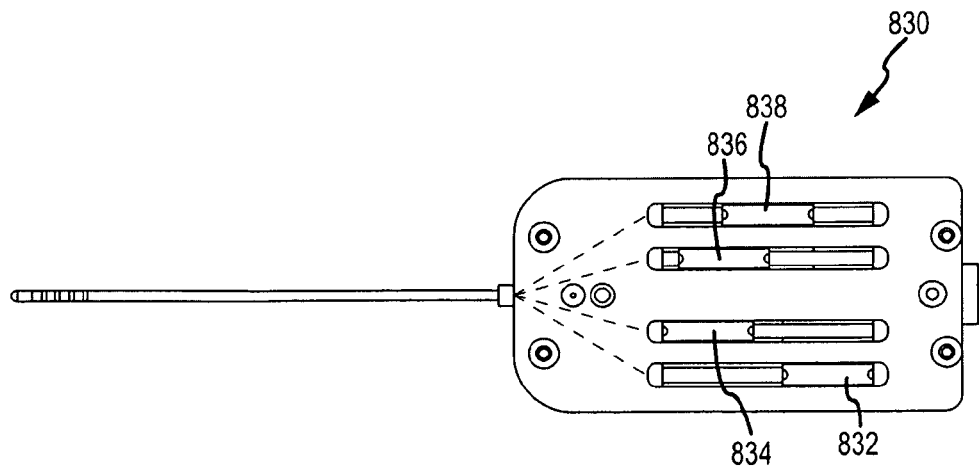

Referring to FIGS. 10a and 10b, a manipulation base 820 includes protruding and linearly movable fingers 822, 824, 826, 828 for operating cartridge 830 including slider blocks 832, 834, 836 and 838. It is conceivable that for the design of mechanism 500 and cartridge drive head 600 discussed above, slider blocks 708, 710 of cartridge 700 may be linearly movable by a mechanism similar to manipulation base 820.

Figure 11A:
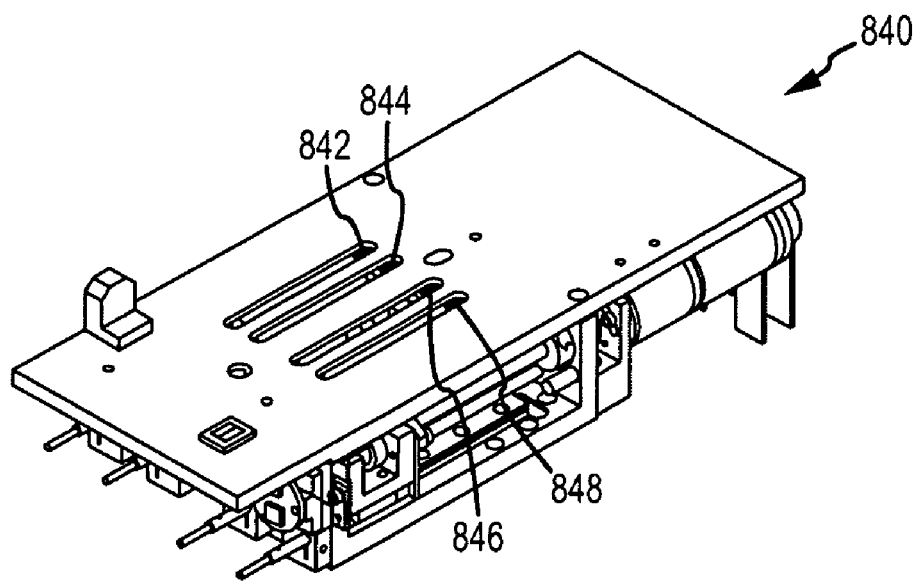
FIGS. 11a and 11b are enlarged isometric views of a fourth embodiment of a robotic catheter manipulation base and robotic catheter device cartridge.
Figure 11B:
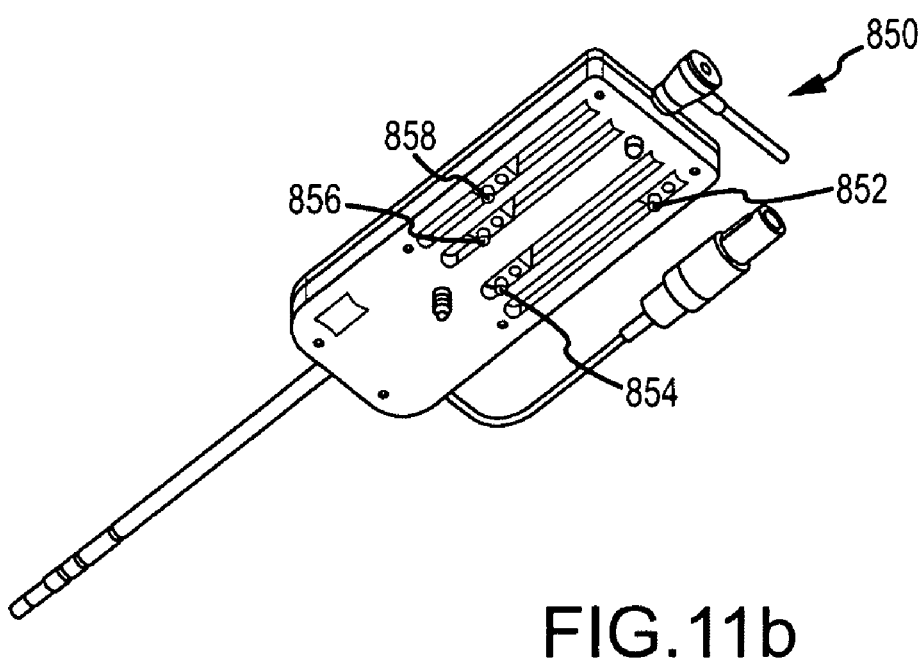

Referring to FIGS. 11a and 11b, a manipulation base 840 includes linearly movable slider blocks 842, 844, 846, 848 for operating cartridge 850 including protruding fingers 852, 854, 856 and 858. It is conceivable that for the design of mechanism 500 and cartridge drive head 600 discussed above, slider blocks 708, 710 of cartridge 700 may be linearly movable by a mechanism similar to manipulation base 840.

The aforementioned electrical handshake between manipulation bases 308, 310 and catheter and sheath cartridges 402, 404, as well as mechanism 500, drive head 600 and cartridge 700 will be described briefly.

Robotic catheter system 10 may be useful for a variety of procedures and in connection with a variety of tools and/or catheters. Such tools and/or catheters may include, without limitation, spiral catheters, ablation catheters, mapping catheters, balloon catheters, needle/dilator tools, cutting tools, cauterizing tools, and/or gripping tools. The system may additionally include a means of identifying the nature and/or type of catheter/tool cartridge that is installed for use, and/or position or connection related information. The system may automatically access/obtain additional information about the cartridge, such as, without limitation, its creation date, serial number, sterilization date, prior uses, etc.

Further, some embodiments of the system may include an ability to "read" or detect the type or nature of the connected cartridge through the use of memory included with the disposable cartridge together with some data/signal transmission means. By way of example, each cartridge may contain a chip (e.g., an EEPROM chip) that can be electrically interfaced by the manipulator head. Such a chip could, for instance, be programmed during the manufacturing process and may electronically store various data, such as the make; model; serial number; creation date; and/or other special features associated with the cartridge or tool. Additionally the chip may contain other worthwhile information, such as an indication of previous use, catheter specific calibration data, and/or any other information that may relate to the safety or performance of the particular device.

Although several embodiments of this invention have been described above with a certain degree of particularity, those skilled in the art could make numerous alterations to the disclosed embodiments without departing from the scope of this invention. All directional references (e.g., upper, lower, upward, downward, left, right, leftward, rightward, top, bottom, above, below, vertical, horizontal, clockwise and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not as limiting. Changes in detail or structure may be made without departing from the invention as defined in the appended claims.

What is claimed is:

1. A robotic catheter rotatable device cartridge having a longitudinal axis, the cartridge comprising:
   a housing member configured for removable attachment to a drive head and a drive mechanism configured to rotate both the cartridge and a catheter attached to the cartridge around the longitudinal axis of the cartridge;
   a first slider block generally slidable relative to the housing along the longitudinal axis, wherein the first slider block is engaged with a first steering wire and is configured for engagement with a first portion of the drive head such that movement of the first portion of the drive head along the longitudinal axis is configured to cause corresponding movement of the first slider block along the longitudinal axis, and wherein the first slider block is configured to move linearly along the longitudinal axis to cause deflection of the catheter in a first direction transverse to the longitudinal axis, and
   a second slider block generally slidable relative to the housing along the longitudinal axis, wherein the second slider block is engaged with a second steering wire and is configured for engagement with a second portion of the drive head such that movement of the second portion of the drive head along the longitudinal axis is configured to cause corresponding movement of the second slider block along the longitudinal axis, and wherein the second slider block is configured to move linearly along the longitudinal axis to cause deflection of the catheter in a second direction transverse to the longitudinal axis, wherein the second direction is different than the first direction.

2. The robotic catheter rotatable device cartridge according to claim 1, further comprising at least one magnetic mount in one of the housing and the drive head for engagement with a complementary surface on the other one of the housing and the drive head for releasable locking of the cartridge with the drive head.

3. The robotic catheter rotatable device cartridge according to claim 1, further comprising at least one recess in one of the housing and the drive head for engagement with at least one complementary locking detent on the other one of the housing and the drive head for releasable locking of the cartridge with the drive head.

4. The robotic catheter rotatable device cartridge according to claim 1, wherein the second direction is generally opposite the first direction.

5. The robotic catheter rotatable device cartridge according to claim 1, wherein the first slider block is linearly driveable to pull the first steering wire generally linearly along a length of the first steering wire and wherein the second slider block is linearly drivable to pull the second steering wire generally linearly along a length of the second steering wire.

6. A robotic catheter rotatable device cartridge having a longitudinal axis, the cartridge comprising:
- a housing member configured for removable attachment to a drive head and a drive mechanism configured to rotate both the cartridge and a surgically insertable device attached to the cartridge around the longitudinal axis of the cartridge;
- a first element generally linearly movable along the longitudinal axis, wherein the first element is engaged with a first steering wire and is configured for engagement with a first portion of the drive head such that movement of the first portion of the drive head along the longitudinal axis is configured to cause corresponding movement of the first element along the longitudinal axis, and wherein the first element is configured to move linearly along the longitudinal axis to cause deflection of the surgically insertable device in a first direction transverse to the longitudinal axis, and
- a second element generally linearly movable along the longitudinal axis, wherein the second element is engaged with a second steering wire and is configured for engagement with a second portion of the drive head such that movement of the second portion of the drive head along the longitudinal axis is configured to cause corresponding movement of the second element along the longitudinal axis, and wherein the second element is configured to move linearly along the longitudinal axis to cause deflection of the surgically insertable device in a second direction transverse to the longitudinal axis, wherein the second direction is different than the first direction.

7. The robotic catheter rotatable device cartridge according to claim 6, further comprising at least one first engageable member on one of the housing and the drive head for engagement with at least one complementary engageable member on the other one of the housing and the drive head for releasable locking of the cartridge with the drive head.

8. The robotic catheter rotatable device cartridge according to claim 6, further comprising at least one magnetic mount in one of the housing and the drive head for engagement with a complementary surface on the other one of the housing and the drive head for releasable locking of the cartridge with the drive head.

9. The robotic catheter rotatable device cartridge according to claim 6, the second direction is generally opposite the first direction.

10. The robotic catheter rotatable device cartridge according to claim 6, wherein the first element is linearly driveable to pull the first steering wire generally linearly along a length of the first steering wire and wherein the second element is linearly drivable to pull the second steering wire generally linearly along a length of the second steering wire.

11. The robotic catheter rotatable device cartridge according to claim 6, wherein the first element is a slider block linearly slidable along a channel on or in the housing.

12. The robotic catheter rotatable device cartridge according to claim 6, wherein the surgically insertable device is one of a catheter, a sheath and a transseptal needle.

13. The robotic catheter rotatable device cartridge according to claim 6, wherein the linear moveability of the first element generally eliminates any backlash or discontinuities during driving of the surgically insertable device.

14. The robotic catheter rotatable device cartridge according to claim 6, wherein the cartridge is infinitely rotatable.

15. The robotic catheter rotatable device cartridge according to claim 6, further comprising integrated force sensors operatively connected to the cartridge for permitting active tensioning of the first steering wire and the second steering wire for controlling deflection of the surgically insertable device.

16. The robotic catheter rotatable device cartridge according to claim 6, further comprising integrated force sensors operatively connected to the cartridge for limiting stress on the surgically insertable device by limiting movement of the cartridge.

* * * * *